(12) United States Patent
Faarup et al.

(10) Patent No.: US 6,884,796 B2
(45) Date of Patent: *Apr. 26, 2005

(54) MEIOSIS REGULATING COMPOUNDS

(75) Inventors: Peter Faarup, Værlose (DK); Frederick Christian Grønvald, Vedbæk (DK); Thorsten Blume, Berlin (DE); Anthony Murray, Hellerup (DK); Jens Breinholt, Søborg (DK)

(73) Assignees: NovoNordisk A/S, Bogsfield (DK); Schering AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/162,843

(22) Filed: Jun. 4, 2002

(65) Prior Publication Data

US 2002/0183283 A1 Dec. 5, 2002

Related U.S. Application Data

(63) Continuation of application No. 09/760,237, filed on Jan. 12, 2001, now Pat. No. 6,407,086, which is a continuation of application No. 09/332,235, filed on Jun. 14, 1999, now abandoned, which is a continuation of application No. PCT/DK99/00263, filed on May 11, 1999.
(60) Provisional application No. 60/092,983, filed on Jul. 16, 1998, and provisional application No. 60/086,306, filed on May 21, 1998.

(30) Foreign Application Priority Data

May 13, 1998 (DK) ........................................ 1998 00657
May 14, 1998 (EP) ............................................ 98250166
Jun. 19, 1998 (DK) ........................................ 1998 00811

(51) Int. Cl.$^7$ .............................................. A61K 31/56
(52) U.S. Cl. ...................................... 514/182; 514/179
(58) Field of Search ................................. 514/182, 179

(56) References Cited

U.S. PATENT DOCUMENTS 6,407,086 B1 * 6/2002 Faarup et al. ............... 514/182

FOREIGN PATENT DOCUMENTS

| | | |
|---|---|---|
| DK | 136909 | 3/1972 |
| DK | 130992 | 8/1972 |
| DK | 158790 B | 5/1980 |
| DK | 162648 B | 8/1980 |
| DK | 146390 B | 1/1981 |
| DK | 156644 B | 10/1982 |
| DK | 159456 B | 11/1982 |
| DK | 165410 B | 7/1983 |
| DK | 156726 B | 9/1983 |
| DK | 165695 B | 11/1984 |
| DK | 167220 B1 | 8/1990 |
| EP | 0 276 823 A2 | 8/1988 |
| FI | 67858 | 6/1980 |
| NO | 144264 | 7/1974 |
| NO | 162562 | 10/1982 |
| NO | 162665 | 10/1982 |
| NO | 158423 | 11/1982 |
| NO | 303450 | 3/1991 |
| SE | 385 905 | 7/1973 |
| SE | 402 462 | 4/1975 |
| SE | 413 247 | 7/1975 |
| SE | 430 508 | 1/1981 |
| WO | WO 94/18225 | 8/1994 |
| WO | WO 96/00235 | 1/1996 |
| WO | WO 96/27658 | 9/1996 |
| WO | WO 97/00884 | 1/1997 |
| WO | WO 98/28323 | 7/1998 |

OTHER PUBLICATIONS

Kandutsch et al., Lipids, vol. 13, No. 10, pp. 704–707 (1978).
Horn et al., Aust. J. Chem., vol. 35, pp. 629–640 (1982).
Wenckens et al., Acta Chemica Scandinavica, vol. 52, pp. 503–507 (1998).
Byskov et al., Nature, vol. 374, pp. 559–562 (1995).
Nes et al., Archives of BioChemistry and BioPhysics, vol. 272, pp. 323–331 (1989).
Levisalles et al., Bulletin De La Societe Chimique De France, No. 6, pp. 2037–2047 (1971).
Ko Arima, Pharmaceutical Bulletin, vol. 1, pp. 224–227 (1953).
Fieser et al., 12.19 Lophenol and 12.20 Citrostadienol, Steroids (1967).
Windaus et al., Uber das Dehydro–cholestenon und seine Hydrierung mit . . . , Justus Liebigs Ann Chem, vol. 542, pp. 218–224 (1939).

* cited by examiner

*Primary Examiner*—Barbara P. Badio
(74) *Attorney, Agent, or Firm*—Len Smith; Reza Green; Richard Bork

(57) ABSTRACT

Certain novel sterol derivatives can be used for regulating the meiosis in oocytes and in male germ cells.

7 Claims, No Drawings

MEIOSIS REGULATING COMPOUNDS

CROSS-REFERENCE TO RELATED APPLICATIONS

This application is a continuation of U.S. Ser. No. 09/760,237, filed Jan. 12, 2001 now U.S. Pat. No. 6,497,086, which is a continuation of U.S. Ser. No. 09/332,235 filed on Jun. 14, 1999, now abandoned, which is a continuation of PCT/DK99/00263 filed on May 11, 1999 and claims priority under 35 U.S.C. 119 of Danish application no. PA 1998 00657 filed on May 13, 1998, Danish application no. PA 1998 00811 filed on Jun. 19, 1998, European application no 98250166.0 filed on May 14, 1998, U.S. provisional application No. 60/086,306 filed on May 21, 1998, and U.S. provisional application No. 60/092,983 filed on Jul. 16, 1998, the contents of which are filly incorporated herein by reference.

FIELD OF THIS INVENTION

The present invention relates to certain pharmacologically active compounds, to pharmaceutical compositions containing certain compounds as active substance and to their use as medicaments. More particularly, it has been found that the derivatives described herein can be used for regulating the meiosis.

BACKGROUND OF THIS INVENTION

Meiosis is the unique and ultimate event of germ cells on which sexual reproduction is based. Meiosis comprises two meiotic divisions. During the first division, exchange between maternal and paternal genes take place before the pairs of chromosomes are separated into the two daughter cells. These contain only half the number (1n) of chromosomes and 2c DNA. The second meiotic division proceeds without a DNA synthesis. This division, therefore, results in the formation of the haploid germ cells with only 1c DNA.

The meiotic events are similar in the male and female germ cells, but the time schedule and the differentiation processes which lead to ova and to spermatozoa differ profoundly. All female germ cells enter the prophase of the first meiotic division early in life, often before birth, but all are arrested as oocytes later in the prophase (dictyate state) until ovulation after puberty. Thus, from early life the female has a stock of oocytes which is drawn upon until the stock is exhausted. Meiosis in females is not completed until after fertilisation, and results in only one ovum and two abortive polar bodies per germ cell. In contrast, only some of the male germ cells enter meiosis from puberty and leave a stem population of germ cells throughout life. Once initiated, meiosis in the male cell proceeds without significant delay and produces 4 spermatozoa.

Only little is known about the mechanisms which control the initiation of meiosis in the male and in the female. In the oocyte, new studies indicate that follicular purines, hypoxanthine or adenosine, could be responsible for meiotic arrest (Downs, S. M. et al. *Dev.Biol.* 82 (1985) 454–458; Eppig, J. J. et al. *Dev. Biol.* 119 (1986) 313–321; and Downs, S. M. *Mol.Reprod.Dev.* 35 (1993), 82–94). The presence of a diffusible meiosis regulating substance was first described by Byskov et al. in a culture system of fetal mouse gonads (Byskov, A. G. et al. in *Dev.Biol.* 52 (1976), 193–200). A meiosis activating substance, (MAS) was secreted by the fetal mouse ovary in which meiosis was ongoing, and a meiosis preventing substance (MPS) was released from the morphologically differentiated testis with resting, non-meiotic germ cells. It was suggested that the relative concentrations of MAS and MPS regulated the beginning, arrest and resumption of meiosis in the male and in the female germ cells (Byskov, A. G. et al. in *The Physiology of Reproduction* (eds. Knobil, E. and Neill, J. D., Raven Press, New York (1994)). Clearly, if meiosis can be regulated, reproduction can be controlled. A recent article (Byskov, A. G. et al. in *Nature* 374 (1995), 559–562) describes the isolation from bull testes and from human follicular fluid of certain sterols that activate oocyte meiosis. Unfortunately, these sterols are rather labile and utilisation of the interesting finding would thus be greatly facilitated if more stable meiosis activating compounds were available.

In *Aust.J.Chem.* 35 (1982), 629–640, Horn et al. deals with compounds possibly having biological activity (insect moulting hormones). Examples of compounds specifically mentioned therein are 5-cyano-5β-cholest-7-en-3-one; 5-cyano-5β-cholest-7-en-3β-ol; 5-methyl-5β-cholest-7-en-3-one; 5-methyl-5β-cholest-7-en-3α-ol; and 5-methyl-5β-cholest-7-en-3β-ol.

In *Bull.Soc.Chim.Fr.* (1971), 2037–2047, Levisalles et al., cholesta-4,8(14)-dien-3-one is described as an intermediate.

In *Just.Lieb.Ann.Chem.* 542 (1939), 218–224, Windaus et al. mentions cholesta-4,7-dien-3-one; cholesta-4,7-dien-3α-ol; and cholesta-4,7-dien-3β-ol as intermediates.

In *Pharm.Bull.* 1 (1953), 224–227, Arima mentions cholesta-4,8-dien-3-one as intermediate.

In *Lipids* 13 (1978), 704 et seq., Kandutsch et al. describes some cholestane derivatives which may be potent inhibitors of sterol synthesis. Compounds specifically mentioned therein are, in FIG. 1, 3β,7α-dihydroxycholest-5-ene; 3β,7β-dihydroxycholest-5-ene; 3β-hydroxycholest-5-en-7-one; 3β-hydroxycholest-7-one; 7α-hydroxycholest-4-en-3-one; in FIG. 2 (compounds 1–5), cholest-3,6-dione; 3β-hydroxycholest-6-one; 3β,6β-dihydroxycholestane; cholest-4-en-3,6-dione; 3β,5α,6β-trihydroxycholestane; in FIG. 3, 3α,5α-dihydroxycholestane; 3β,4β-dihydroxycholest-5-ene; and, in FIG. 4 (compounds 1, 3, 4 and 5), cholest-2-en-6-one; cholest-4,6-dien-3-one; cholest-4,7-dien-3-one; cholest-3,5-dien-7-one.

Danish patent application with publication number 130,992, deals with compounds possibly having progestomimetic properties. Examples of compounds specifically mentioned therein are 19-nor-21-methylpregna-4,9-dien-17α-hydroxy-3,20-dione; 19-nor-21-methyl-pregna-4,9-dien-17α-acetoxy-3,20-dione; 19-nor-21,21-dimethylpregna-4,9-diene-17α-hydroxy-3,20-dione; and 17α-21,21-dimethyl-19-nor-pregna-4,9-dien-3,20-dione.

In the Danish patent application with publication number 136,909, 3α-acetoxy-24-nor-cholan-23-one; 3α-hydroxy-26,27-di-nor-23-trans-5β-cholest-23-en-25-carboxylic acid methyl ester; 3α-hydroxy-26,27-di-nor-5 β-cholesta-25-carboxylic acid methyl ester; 3-keto-26,27-di-nor-5β-cholesta-25-carboxylic acid methyl ester; 3-keto-4-bromo-26,27-di-nor-5β-cholesta-25-carboxylic acid methyl ester; 3-keto-26,27-di-nor-cholest-4-en-25-carboxylic acid methyl ester; 3β-acetoxy-26,27-di-nor-cholesta-3,5-dien-25-carboxylic acid methyl ester; 3β-hydroxy-26,27-di-nor-cholest-5-en-25-carboxylic acid methyl ester; 3-keto-26,27-di-nor-cholest-4,6-dien-25-carboxylic acid methyl ester; 3β-hydroxy-26,27-di-nor-cholesta-3,5,7-trien-25-carboxylic acid methyl ester; and 3β-hydroxy-26,27-di-nor-cholesta-5,7-dien-25-carboxylic acid methyl ester are mentioned as intermediates.

Danish patent application with publication number 146,390, deals with compounds possibly having pharmacological properties, e.g. an inhibiting action on the production of serum cholesterol. Examples of compounds specifically mentioned therein are 3β,22-di-acetoxycholesta-5-en-25-ol; 3β,22-diacetoxy-25-fluorocholesta-5-ene; 22-hydroxycholesta-5-en-25-fluoro-30-hemisuccinate; 3β,22-diacetoxy-25-dichlorocholesta-5-ene; 3β,22-dihydroxy-25-chlorocholesta-5-ene; 22-hydroxy-25-chlorocholesta-5-en-3β-hemisuccinate; 3β,22-dihydroxy-25-bromocholesta-5-ene; and 3β,22-dihydroxy-25-fluorocholesta-5-ene.

In the Danish patent applications with publication numbers 156,726 and 156,644, cholenic acid; 3β-acetoxycholesta-5-en-25-des-dimethyl-24-one; 3,24-diacetoxycholesta-25-des-dimethyl-5,23-diene; 3β-acetoxycholesta-25-des-methyl-5-en-24-difluoro-25-one; and 3β-acetoxy-24-difluorocholesta-5,7-dien-25-ol are mentioned as intermediates.

In the Danish patent application with publication number 158,790, 3>hydroxycholest-5-en-24-one; 3β-acetoxycholest-5-en-24-one; 5β-cholest-24-one; 5β-cholestan-24α-homo-24-one; 3β,6α-dihydroxy-5β-cholest-24-one; 3α,6α-diacetoxy-5β-cholest-24-one; 3α,6α-diacetoxy-5β-cholest-24α-homo-24-one; 3α,6α-dihydroxy-5β-cholest-24α,24-24-one; 3α-hydroxy-5β-cholest-24-one; 3α-acetoxy-5β-cholesta-24-one; 3α-benzoyl-5β-cholesta-24-one; 3α-ethyloxycarbonyloxy-5β-cholesta-24-one; 3α-hydroxy-5β-cholestan-24α-homo-24-one; 3α-hydroxy-24α,24β-bis-homo-5β-cholestane; 3β-hydroxycholesta-5,7-dien-24-one; 3β-acetoxycholesta-5,7-dien-24-one; 1α,3β-dihydroxycholesta-5,7-diene-24-one; and 1α,3β-diacetoxycholesta-5,7-diene-24-one are mentioned as intermediates.

Danish patent application with publication number 159,456, deals with compounds possibly having utility in the treatment of gall diskinese. Examples of compounds specifically mentioned therein are chenodeoxycholic acid; ursodeoxycholic acid; trimebutyn salt of chenodeoxycholic acid; and trimebutyn salt of ursodeoxycholic acid.

In the Danish patent application with publication number 162,648, 3β,25-dihydroxycholest-5-en-24-one; 3β-acetoxycholest-5-en-24-one; 3β-acetoxy-25-hydroxycholest-5-en-24-one; 3β,25-dihydroxycholest-5-en-24-one; 3β-hydroxycholest-5-en-24-one; 3β-hydroxy-25-hydroperoxycholest-5-en-24-one; 3β,24,25-trihydroxycholest-5-ene; 1α,3β-dihydroxycholest-5-en-24-one; 1α,3β,25-trihydroxycholest-5-en-24-one; 1α,3β,24,25-tetrahydroxycholest-5-en-24-one are mentioned as intermediates.

In the Danish patent application with publication number 165,410, 3β-acetoxy-7α-bromocholest-5-ene; 3α-acetoxycholesta-5,7-diene; and 3α-acetoxy-25-hydroxycholesta-5,7-diene are mentioned as intermediates.

In the Danish patent application with publication number 165,695, 3β,25-dihydroxy-26,27-hexafluorocholest-5-ene; and 1α,3β,25-trihydroxy-26,27-hexafluorocholest-5-ene are mentioned as intermediates for the preparation of vitamin D analogues.

Danish patent application with publication number 167,220 deals with compounds possibly having utility for the treatment of liver disorders. An examples of a compound specifically mentioned therein is 3α,7α,12α,24β,26,27-hexahydroxycholestane.

In U.S. Pat. No. 4,425,274, the compounds 3α-hydroxy-7-cholanic acid; 3α,7α-dihydroxycholanic acid; 3α,7β-dihydroxycholanic acid; and lithium 3α,7α-dihydroxycholanate are described as intermediates.

In the Norwegian patent application with publication number 144,264, cholesta-1,4,-6-trien-3-one; cholest-5-en-1α,3β-diol; 1α-hydroxycholesta-4,6-diene-3-one; 1α,3β-di-hydroxycholest-5-ene; 25-hydroxycholesta-1,4,6-triene-3-one; and 1α,3β-25-trihydroxycholest-5-ene are mentioned as intermediates for the preparation of 1α-hydroxy steroids of the cholestane serie.

Norwegian patent application with publication number 158,423, deals with compounds possibly having utility in the treatment of biliary dyskinesis. An example of a compound specifically mentioned therein is 3α,7β-dihydroxydeoxycholic acid.

In the Norwegian patent application with publication number 162,562, 3α,7β-dihydroxydeoxycholic acid; 7-ketodeoxycholic acid; 3α,7β-dihydroxydeoxycholic acid; cholic acid; 7-ketocholic acid; 3α,7β,12α-cholic acid; and 12-ketocholic acid are mentioned as being intermediates in the preparation of ursodeoxycholanic acid.

In the Norwegian patent application with publication number 162,665, cholic acid; 3α-hydroxy-7-ketocholic acid; 3α,7α-diacetoxycholic acid; 3α,7α-diacetoxy-12-ketocholic acid; 3α,7α-dihydroxydeoxycholic acid; 7-ketodeoxycholic acid; 3α,7β-dihydroxydeoxycholic acid; and 3α,7β-dihydroxy-12-ketocholic acid are mentioned as being intermediates in the preparation of ursodeoxycholanic acid.

In the Norwegian patent application with publication number 303,450, cholic acid; cholic acid methyl ester; 3-acetylcholic acid methyl ester; 3-(2-propenyl)cholic acid methyl ester; 3-(3-hydroxypropyl)cholic acid-3-methyl ester; desoxycholic acid; 12-keto-desoxycholic acid; 3β-acetyloxy-12-keto-desoxycholic acid; 3β-(hydroxyethyloxy)cholic acid methyl ester; 3β-(hydroxypropyloxy)cholic acid methyl ester; 3β-(hydroxybutyloxy)cholic acid methyl ester; 3β-(hydroxyentyloxy)cholic acid methyl ester; 3β-(hydroxyhexyloxy)cholic acid methyl ester; 3β-(hydroxydecanoyloxy)cholic acid methyl ester; 3β-(2-hydroxyethyloxyethyloxy)cholic acid methyl ester; 3β-(2-hydroxypropyloxy)cholic acid methyl ester; 3β-(hydroxy-ethyloxy)desoxycholic acid methyl ester; 3β-(hydroxypropyloxy)desoxycholic acid methyl ester; 3β-(hydroxypentyloxy)desoxycholic acid methyl ester; 3β-(hydroxydecyloxy)desoxy-cholic acid methyl ester, 3β-(2-hydroxyethyloxy)chenodesoxycholic acid methyl ester; 3β-(3-hydroxypropyloxy) chenodesoxycholic acid methyl ester; 3β-(5-hydroxypentyloxy)chenodesoxycholic acid methyl ester; 3β-(10-hydroxydecyloxy)chenodesoxycholic acid methyl ester; 3β-(2-hydroxyethyloxy)litocholic acid methyl ester; 3β-(3-hydroxypropyloxy)litocholic acid methyl ester; 3β-(5-hydroxypenthyloxy)lithocholic acid methyl ester; 3β-(10-hydroxydecayloxy)lithocholic acid methyl ester; 3β-(benzyloxyethyloxy)cholic acid methyl ester; 3β-(benzyloxyethyloxy)cholic acid tert.butyl ester; 3β-(2-hydroxyethyloxy)cholic acid tert.butyl ester; 3β-(2-hydroxyethyloxy)-7α, 12α-diacetyloxycholic acid methyl ester; and 3β-(propionyloxy)-7α,12α-diacetyloxy-24-carboxylic acid methyl ester are mentioned as intermediates.

In the Swedish patent application with publication number 385,905, chenodeoxy-cholic acid is mentioned to have utility for the treatment of cholelithiasis and cholic acid is mentioned as an intermediate for the preparation thereof.

Swedish patent application with publication number 402,462 mentions sitosterol which may have medical application, e.g. for the prevention or reduction of absorption of cholesterol in the small intestine, and campesterol is mentioned to lower the effect of sitosterol.

In the Swedish patent application with publication number 413,247, 3α-hydroxycholestane and 3β-hydroxycholestane are mentioned to have antiinflammatoric properties and slightly side effects.

Swedish patent application with publication number 430,508 deals with compounds possibly having pharmacological properties, i.e. inhibition of HMG-CoA reductase and inhibition of the formation of serum cholesterol. Examples of compounds specifically mentioned therein are 25-fluorocholest-5-en-3β,22-diol; 25-chlorocholest-5-en-3β,22-diol; 22-hydroxy-25-fluorocholest-5-en-3β-hemisuccinate; 22-hydroxy-25-chlorocholest-5-en-3β-hemisuccinate; and cholesta-5-en-3β,22,25-triol.

Compounds being known to stimulate the meiosis and being different from the compounds claimed in the present patent application are described in International patent applications having Nos. WO 96/00235, 96127658 and 97/00884 (Novo Nordisk A/S) and 98/55498. In International patent application having No. WO 98/52965, filed on May 11, 1998 and published on Nov. 26, 1998, it is stated that certain 20-aralkyl-5α-pregnan derivatives can be used in the preparation of a medicament for the control of fertility and some of the specific compounds mentioned therein are (3β,5α,20R)-4,4,20-trimethyl-21-phenylpregna-8,14-dien-3-ol (example 1); (3β,5α,20R)-4,4,20-trimethyl-21-(3-methylphenyl)pregna-8,14-dien-3-ol (example 2A); and (3β,5α,20R), 4-dimethyl-23-phenyl-24-norchola-8,14-dien-3-ol (example 7A).

The compounds described herein have advantages compared with the known compounds.

SUMMARY OF THIS INVENTION

A main purpose of this invention is to furnish compounds which can be used to regulate meiosis.

One purpose of the present invention is to provide compounds and methods useful for relieving infertility in females and males, particularly in mammals, more particularly in humans.

In a further object, the present invention concerns the use of the compounds of the general formula Ic (stated in the claims, below) for relieving infertility in females and males, particularly in mammals, more particularly in humans.

In a further object of the present invention the compounds of the general formula I are useful as contraceptives in females and males, particularly in mammals, more particularly in humans.

In another embodiment, the invention relates to esters, salts, active metabolites and prodrugs of compound of the general formula Ia.

In still another preferred embodiment, the present invention relates to compounds of the general formula Ib (stated in the claims below) or esters, salts, active metabolites or prodrugs thereof as a medicament.

In a further preferred embodiment, this invention relates to compounds of the general formula Ic (stated in the claims below) or esters, salts, active metabolites or prodrugs thereof in the manufacture of a medicament for use in the regulation of meiosis.

In a further preferred aspect, the present invention relates to the use of a compound of formula Ib/Ic or an ester, salt, active metabolite or prodrug thereof as a medicament, in particular as a medicament for use in the regulation of meiosis. The compound may be used neat or in the form of a liquid or solid composition containing auxiliary ingredients conventionally used in the art.

In the present context, the expression "regulating the meiosis" is used to indicate that certain of the compounds of formula Ia, Ib or Ic can be used for stimulating the meiosis in vitro, in vivo, or ex vivo. Thus, the compounds of formula Ia, Ib or Ic which may be agonists of a naturally occurring meiosis activating substance, can be used in the treatment of infertility which is due to insufficient stimulation of meiosis in females and in males. Other compounds of formula Ia, Ib or Ic, which may be antagonists of a naturally occurring meiosis activating substance, can be used for regulating the meiosis, preferably in vivo, in a way which makes them suited as contraceptives. In this case the "regulation" means partial or total inhibition.

In a still further preferred aspect, the present invention relates to the use of a compound of formula Ic or an ester, salt, active metabolite or prodrug thereof in the regulation of the meiosis of an oocyte, in particular a mammalian oocyte, more particularly a human oocyte.

In a still further preferred aspect, the present invention relates to the use of a compound of formula Ic or an ester, salt, active metabolite or prodrug thereof in the stimulation of the meiosis of an oocyte, in particular a mammalian oocyte, more particularly a human oocyte.

In a still further preferred aspect, the present invention relates to the use of a compound of formula Ic or an ester, salt, active metabolite or prodrug thereof in the inhibition of the meiosis of an oocyte, in particular a mammalian oocyte, more particularly a human oocyte.

In a still further preferred aspect, the present invention relates to the use of a compound of formula Ic or an ester, salt, active metabolite or prodrug thereof in the regulation of the meiosis of a male germ cell, in particular a mammalian male germ cell, more particularly a human male germ cell.

In a still further preferred aspect, the present invention relates to the use of a compound of formula Ic or an ester, salt, active metabolite or prodrug thereof in the stimulation of the meiosis of a male germ cell, in particular a mammalian male germ cell, more particularly a human male germ cell.

In a still further preferred aspect, the present invention relates to the use of a compound of formula Ic or an ester, salt, active metabolite or prodrug thereof in the inhibition of the meiosis of a male germ cell, in particular a mammalian male germ cell, more particularly a human male germ cell.

In a yet still further preferred aspect, the present invention relates to a method of regulating the meiosis in a mammalian germ cell which method comprises administering an effective amount of a compound of formula Ic or an ester, salt, active metabolite or prodrug thereof to a germ cell in need of such a treatment.

In a still further aspect, the present invention relates to a method of regulating the meiosis in a mammalian germ cell wherein a compound of formula Ic or an ester, salt, active metabolite or prodrug thereof is administered to the germ cell by administering the compound to a mammal hosting said cell.

In a still further aspect, the present invention relates to a method wherein the germ cell the meiosis of which is to be regulated by means of a compound of formula Ic or an ester, salt, active metabolite or prodrug thereof is an oocyte.

In a still further aspect, the present invention relates to a method of regulating the meiosis in an oocyte wherein a compound of formula Ic or an ester, salt, active metabolite or prodrug thereof is administered to the oocyte ex vivo.

In a still further aspect, the present invention relates to a method of regulating the meiosis of a male germ cell by administering a compound of formula Ic or an ester, salt, active metabolite or prodrug thereof to the cell.

In a still further aspect, the present invention relates to a method whereby mature male germ cells are produced by administering in vivo or in vitro a compound of formula Ic or an ester, salt, active metabolite or prodrug thereof to testicular tissue containing immature cells.

In a still further aspect, the present invention relates to compounds of formula Ia, Ib and Ic having improved stability.

According to the present invention there are provided novel compounds of formula Ia (stated in claim 1, below) with interesting pharmacological properties. The compounds described herein are useful for regulating the meiosis in oocytes and in male germ cells.

DETAILED DESCRIPTION OF THIS INVENTION

It has, surprisingly, been found that compounds having a side chain ($R^{22}$) which is different from the cholesterol and lanosterol side chains or compounds having certain specifically elected substituents in the ring system, have superior properties.

Preferred compounds of formula Ia, Ib and Ic are such having a double bond.

Other preferred compounds of formula Ia, Ib and Ic are such wherein $R^1$ is hydrogen.

Other preferred compounds of formula Ia, Ib and Ic are such wherein $R^1$ is halogen.

Other preferred compounds of formula Ia, Ib and Ic are such wherein $R^1$ is methyl.

Other preferred compounds of formula Ia, Ib and Ic are such wherein $R^1$ is hydroxy Other preferred compounds of formula Ia, Ib and Ic are such wherein $R^1$ is oxo.

Other preferred compounds of formula Ia, Ib and Ic are such wherein $R^2$, together with $R^3$, designates an additional bond between the carbon atoms at which $R^2$ and $R^3$ are placed.

Other preferred compounds of formula Ia, Ib and Ic are such wherein $R^2$ is hydrogen.

Other preferred compounds of formula Ia, Ib and Ic are such wherein $R^2$ is hydroxy.

Other preferred compounds of formula Ia, Ib and Ic are such wherein $R^2$ is $C_1$–$C_3$ alkyl.

Other preferred compounds of formula Ia, Ib and Ic are such wherein $R^2$ is $C_1$–$C_3$ alkoxy.

Other preferred compounds of formula Ia, Ib and Ic are such wherein $R^2$ is halogen.

Other preferred compounds of formula Ia, Ib and Ic are such wherein $R^3$ is hydrogen.

Other preferred compounds of formula Ia, Ib and Ic are such wherein $R^3$ is hydroxy.

Other preferred compounds of formula Ia, Ib and Ic are such wherein $R^3$ is alkoxy, aralkyloxy, alkoxyalkoxy or alkanoyloxyalkyl, each group comprising a total of up to 10 carbon atoms, preferably up to 8 carbon atoms.

Other preferred compounds of formula Ia, Ib and Ic are such wherein $R^3$ is $C_1$–$C_4$ alkoxy.

Other preferred compounds of formula Ia, Ib and Ic are such wherein $R^3$ is methoxy.

Other preferred compounds of formula Ia, Ib and Ic are such wherein $R^3$ is ethoxy.

Other preferred compounds of formula Ia, Ib and Ic are such wherein $R^3$ is $CH_3OCH_2O$—.

Other preferred compounds of formula Ia, Ib and Ic are such wherein $R^3$ is pivaloyloxymethoxy.

Other preferred compounds of formula Ia, Ib and Ic are such wherein $R^3$ is an acyloxy group derived from an acid having from 1 to 20 carbon atoms.

Other preferred compounds of formula Ia, Ib and Ic are such wherein $R^3$ is an acyloxy group selected from the group comprising acetoxy, benzoyloxy, pivaloyloxy, butyryloxy, nicotinoyloxy, isonicotinoyloxy, hemi succinoyloxy, hemi glutaroyloxy, butylcarbamoyloxy, phenylcarbamoyloxy, butoxycarbonyloxy, tert-butoxycarbonyloxy and ethoxycarbonyloxy.

Other preferred compounds of formula Ia, Ib and Ic are such wherein $R^3$ is sulphonyloxy.

Other preferred compounds of formula Ia, Ib and Ic are such wherein $R^3$ is phosphonyloxy.

Other preferred compounds of formula Ia, Ib and Ic are such wherein $R^3$ together with $R^3$ is oxo.

Other preferred compounds of formula Ia, Ib and Ic are such wherein $R^3$ is the group =NOH.

Other preferred compounds of formula Ia, Ib and Ic are such wherein $R^3$ is a group of the general formula =$NOR^{38}$, wherein $R^{38}$ is $C_1$–$C_3$ alkyl.

Other preferred compounds of formula Ia, Ib and Ic are such wherein $R^3$ is halogen.

Other preferred compounds of formula Ia, Ib and Ic are such wherein $R^3$ is hydroxy and $C_1$–$C_4$ alkyl bound to the same carbon atom of the sterol skeleton.

Other preferred compounds of formula Ia, Ib and Ic are such wherein $R^3$ is perfluoro-(lower alkyl), preferably perfluoro(lower alkyl) having 1 through 6, preferably 1 through 3, carbon atoms in the alkyl group, more preferred trifluoromethyl.

Other preferred compounds of formula Ia, Ib and Ic are such wherein $R^4$ and $R^{14}$ are both hydrogen.

Other preferred compounds of formula Ia, Ib and Ic are such wherein one of $R^4$ and $R^{14}$ is hydrogen while the other is methyl.

Other preferred compounds of formula Ia, Ib and Ic are such wherein $R^4$ and $R^{14}$ are both methyl.

Other preferred compounds of formula Ia, Ib and Ic are such wherein $R^4$ is branched or unbranched $C_1$–$C_5$ alkyl, optionally substituted by halogen, hydroxy or cyano.

Other preferred compounds of formula Ia, Ib and Ic are such wherein $R^{14}$ is branched or unbranched $C_1$–$C_6$ alkyl, optionally substituted by halogen, hydroxy or cyano.

Other preferred compounds of formula Ia, Ib and Ic are such wherein $R^4$ is hydroxy and $R^4$ is selected from the group comprising hydrogen and branched or unbranched $C_1$–$C_5$ alkyl which may be substituted by halogen, hydroxy or cyano.

Other preferred compounds of formula Ia, Ib and Ic are such wherein $R^{14}$ is hydroxy and $R^4$ is selected from the group comprising hydrogen and branched or unbranched $C_1$–$C_6$ alkyl which may be substituted by halogen, hydroxy or cyano.

Other preferred compounds of formula Ia, Ib and Ic are such wherein $R^4$ and $R^{14}$ together designate methylene.

Other preferred compounds of formula Ia, Ib and Ic are such wherein $R^4$ and $R^{14}$, together with the carbon atom to which they are bound, form a cyclopropane ring.

Other preferred compounds of formula Ia, Ib and Ic are such wherein $R^4$ and $R^{14}$, together with the carbon atom to which they are bound, form a cyclopentane ring.

Other preferred compounds of formula Ia, Ib and Ic are such wherein $R^4$ and $R^{14}$, together with the carbon atom to which they are bound, form a cyclohexane ring.

Other preferred compounds of formula Ia, Ib and Ic are such wherein $R^5$ is hydrogen.

Other preferred compounds of formula Ia, Ib and Ic are such wherein $R^5$ is halogen.

Other preferred compounds of formula Ia, Ib and Ic are such wherein $R^5$ is hydroxy.

Other preferred compounds of formula Ia, Ib and Ic are such wherein $R^5$ is alkyl with 1 through 3 carbon atoms, preferably methyl, cyano or hydroxymethyl, or $R^5$ is, together with $R^4$, a methano bridge or $R^5$ is, together with $R^4$, an additional bond.

Other preferred compounds of formula Ia, Ib and Ic are such wherein $R^5$ is a primary or secondary amide derived from a carboxylic acid.

Other preferred compounds of formula Ia, Ib and Ic are such wherein $R^5$ is an ester with a $C_1$–$C_6$-alcohol group.

Other preferred compounds of formula Ia, Ib and Ic are such wherein $R^6$ is hydrogen.

Other preferred compounds of formula Ia, Ib and Ic are such wherein $R^6$ is halogen.

Other preferred compounds of formula Ia, Ib and Ic are such wherein $R^6$ is oxo.

Other preferred compounds of formula Ia, Ib and Ic are such wherein $R^6$ is hydroxy.

Other preferred compounds of formula Ia, Ib and Ic are such wherein $R^6$, together with $R^5$, designates an additional bond between the carbon atoms at which $R^5$ and $R^6$ are placed.

Other preferred compounds of formula Ia, Ib and Ic are such wherein $R^7$ is hydrogen.

Other preferred compounds of formula Ia, Ib and Ic are such wherein $R^7$ is hydrogen.

Other preferred compounds of formula Ia, Ib and Ic are such wherein $R^7$ is methoxy or acetoxy.

Other preferred compounds of formula Ia, Ib and Ie are such wherein $R^7$ is hydroxy or acetoxy.

Other preferred compounds of formula Ia, Ib and Ic are such wherein $R^7$ is halogen.

Other preferred compounds of formula Ia, Ib and Ic are such wherein $R^7$ is oxo.

Other preferred compounds of formula Ia, Ib and Ic are such wherein $R^7$ is the group =NOH.

Other preferred compounds of formula Ia, Ib and Ic are such wherein $R^7$ is a group of the general formula =$NOR^{36}$, wherein $R^{36}$ is $C_1$–$C_3$ alkyl.

Other preferred compounds of formula Ia, Ib and Ic are such wherein $R^7$ simultaneously is hydroxy and $C_1$–$C_4$ alkyl both being bound to the same carbon atom of the sterol skeleton, i.e. in the 7 position.

Other preferred compounds of formula Ia, Ib and Ic are such wherein $R^7$, together with $R^9$, designates an additional bond between the carbon atoms at which $R^7$ and $R^6$ are placed.

Other preferred compounds of formula Ia, Ib and Ic are such wherein $R^7$, together with $R^8$, designates an additional bond between the carbon atoms at which $R^7$ and $R^8$ are placed.

Other preferred compounds of formula Ia, Ib and Ic are such wherein $R^8$, together with $R^9$, designates an additional bond between the carbon atoms at which $R^8$ and $R^9$ are placed.

Other preferred compounds of formula Ia, Ib and Ic are such wherein $R^8$ is hydrogen.

Other preferred compounds of formula Ia, Ib and Ic are such wherein $R^8$ is halogen.

Other preferred compounds of formula Ia, Ib and Ic are such wherein $R^8$ is hydroxy.

Other preferred compounds of formula Ia, Ib and Ic are such wherein $R^9$ is hydrogen.

Other preferred compounds of formula Ia, Ib and Ic are such wherein $R^9$ is halogen.

Other preferred compounds of formula Ia, Ib and Ic are such wherein $R^9$ is hydroxy.

Other preferred compounds of formula Ia, Ib and Ic are such wherein $R^{11}$ is hydrogen.

Other preferred compounds of formula Ia, Ib and Ic are such wherein $R^{11}$ is methylene.

Other preferred compounds of formula Ia, Ib and Ic are such wherein $R^{11}$ is hydroxy.

Other preferred compounds of formula Ia, Ib and Ic are such wherein $R^{11}$ is halogen.

Other preferred compounds of formula Ia, Ib and Ic are such wherein $R^{11}$ is methoxy or acetoxy.

Other preferred compounds of formula Ia, Ib and Ic are such wherein $R^{11}$ is oxo.

Other preferred compounds of formula Ia, Ib and Ic are such wherein $R^{11}$ is the group =NOH.

Other preferred compounds of formula Ia, Ib and Ic are such wherein $R^{11}$ is a group of the general formula =$NOR^{37}$, wherein $R^{37}$ is $C_1$–$C_3$ alkyl.

Other preferred compounds of formula Ia, Ib and Ic are such wherein $R^{11}$ simultaneously is hydroxy and $C_1$–$C_4$ alkyl both being bound to the same carbon atom of the sterol skeleton, i.e. in the 11 position.

Other preferred compounds of formula Ia, Ib and Ic are such wherein $R^{11}$, together with $R^9$, designates an additional bond between the carbon atoms at which $R^{11}$ and $R^9$ are placed.

Other preferred compounds of formula Ia, Ib and Ic are such wherein $R^{11}$, together with $R^{12}$, designates an additional bond between the carbon atoms at which $R^{11}$ and $R^{12}$ are placed.

Other preferred compounds of formula Ia, Ib and Ic are such wherein $R^{12}$ is hydrogen.

Other preferred compounds of formula Ia, Ib and Ic are such wherein $R^{12}$ is halogen.

Other preferred compounds of formula Ia, Ib and Ic are such wherein $R^{12}$ is $C_1$–$C_4$ alkyl.

Other preferred compounds of formula Ia, Ib and Ic are such wherein $R^{12}$ is methylene.

Other preferred compounds of formula Ia, Ib and Ic are such wherein $R^{12}$ is hydroxy.

Other preferred compounds of formula Ia, Ib and Ic are such wherein $R^{12}$ is methoxy or acetoxy.

Other preferred compounds of formula Ia, Ib and Ic are such wherein $R^{12}$ is oxo.

Other preferred compounds of formula Ia, Ib and Ic are such wherein $R^{12}$ is the group =NOH.

Other preferred compounds of formula Ia, Ib and Ic are such wherein R12 is a group of the general formula =$NOR^{33}$, wherein $R^{33}$ is $C_1$–$C_3$ alkyl.

Other preferred compounds of formula Ia, Ib and Ic are such wherein $R^{14}$ is hydrogen.

Other preferred compounds of formula Ia, Ib and Ic are such wherein $R^{14}$ is hydroxy.

Other preferred compounds of formula Ia, Ib and Ic are such wherein $R^{14}$, together with $R^8$, designates an additional bond between the carbon atoms at which $R^{14}$ and $R^a$ are placed.

Other preferred compounds of formula Ia, Ib and Ic are such wherein $R^{15}$ is hydrogen.

Other preferred compounds of formula Ia, Ib and Ic are such wherein $R^{15}$ is halogen.

Other preferred compounds of formula Ia, Ib and Ic are such wherein $R^{15}$ is $C_1$–$C_4$ alkyl.

Other preferred compounds of formula Ia, Ib and Ic are such wherein $R^{15}$ is methylene.

Other preferred compounds of formula Ia, Ib and Ic are such wherein $R^{15}$ is hydroxy.

Other preferred compounds of formula Ia, Ib and Ic are such wherein $R^{15}$ is methoxy.

Other preferred compounds of formula Ia, Ib and Ic are such wherein $R^{15}$ is oxo.

Other preferred compounds of formula Ia, Ib and Ic are such wherein $R^{15}$ is the group =NOH.

Other preferred compounds of formula Ia, Ib and Ic are such wherein $R^{15}$ is a group of the general formula =$NOR^{32}$, wherein $R^{32}$ is $C_1$–$C_3$ alkyl.

Other preferred compounds of formula Ia, Ib and Ic are such wherein $R^1$, together with $R^{14}$, designates an additional bond between the carbon atoms at which $R^{15}$ and $R^{14}$ are placed.

Other preferred compounds of formula Ia, Ib and Ic are such wherein $R^{16}$ is hydrogen.

Other preferred compounds of formula Ia, Ib and Ic are such wherein $R^{16}$ is halogen.

Other preferred compounds of formula Ia, Ib and Ic are such wherein $R^{16}$ is $C_1$–$C_3$ alkyl.

Other preferred compounds of formula Ia, Ib and Ic are such wherein $R^{16}$ is methylene.

Other preferred compounds of formula Ia, Ib and Ic are such wherein $R^{16}$ is hydroxy.

Other preferred compounds of formula Ia, Ib and Ic are such wherein $R^{16}$ is methoxy.

Other preferred compounds of formula Ia, Ib and Ic are such wherein $R^{16}$ is oxo.

Other preferred compounds of formula Ia, Ib and Ic are such wherein $R^{16}$ is the group =NOH.

Other preferred compounds of formula Ia, Ib and Ic are such wherein $R^{16}$ is a group of the general formula =$NOR^{34}$, wherein $R^{34}$ is $C_1$–$C_3$ alkyl.

Other preferred compounds of formula Ia, Ib and Ic are such wherein $R^{16}$ together with $R^{17}$, designates an additional bond between the carbon atoms at which $R^{16}$ and $R^{17}$ are placed.

Other preferred compounds of formula Ia, Ib and Ic are such wherein $R^{17}$ is hydrogen.

Other preferred compounds of formula Ia, Ib and Ic are such wherein $R^{17}$ is hydroxy.

Other preferred compounds of formula Ia, Ib and Ic are such wherein $R^{17}$ is in the a position.

Other preferred compounds of formula Ia, Ib and Ic are such wherein $R^{20}$ is hydrogen.

Other preferred compounds of formula Ia, Ib and Ic are such wherein $R^{20}$ is hydroxymethyl.

Other preferred compounds of formula Ia, Ib and Ic are such wherein $R^{20}$ is $C_1$–$C_4$ alkyl.

Other preferred compounds of formula Ia, Ib and Ic are such wherein $R^{20}$ together with $R'^{20}$ designates methylene.

Other preferred compounds of formula Ia, Ib and Ic are such wherein $R^{20}$ together with $R'^{20}$ designates oxo.

Other preferred compounds of formula Ia, Ib and Ic are such wherein $R'^{20}$ is hydrogen.

Other preferred compounds of formula Ia, Ib and Ic are such wherein $R'^{20}$ is halogen.

Other preferred compounds of formula Ia, Ib and Ic are such wherein $R'^{20}$ is methyl.

Other preferred compounds of formula Ia, Ib and Ic are such wherein $R'^{20}$ is hydroxy.

Other preferred compounds of formula Ia, Ib and Ic are such wherein $R^{22}$ is cyclohexyl optionally substituted by one or more of the following groups which substituents may be different or identical: hydroxy, alkoxy, halogen, amino, cyano, carboxy, a group of the general formula —$COOR^{39}$, oxo, N-alkylamino or N,N-dialkylamino wherein the N-alkylamino or N,N-dialkylamino substituent optionally is substituted by carboxy, lower alkoxy or lower alkylthio; cyclohexylalkyl optionally substituted by one or more of the following groups which substituents may be different or identical: hydroxy, lower alkoxy, halogen, amino, cyano, carboxy, a group of the general formula —$COOR^{39}$, oxo, N-alkylamino or N,N-dialkylamino wherein the N-alkylamino or N,N-dialkylamino substituent optionally is substituted by carboxy, lower alkoxy or lower alkylthio;

alkyl optionally substituted by one or more of the following groups which substituents may be different or identical: hydroxy, alkoxy, halogen, amino, cyano, carboxy, a group of the general formula —$COOR^{39}$, oxo, N-acylamino, N-alkylamino or N,N-dialkylamino wherein the N-alkylamino or N,N-dialkylamino substituent optionally is substituted by carboxy, lower alkoxy or lower alkylthio; or alkenyl optionally substituted by one or more of the following groups which substituents may be different or identical: hydroxy, lower alkoxy, halogen, amino, cyano, carboxy, a group of the general formula —$COOR^{39}$, oxo, N-alkylamino or N,N-dialkylamino wherein the N-alkylamino or N,N-dialkylamino substituent optionally is substituted by carboxy, lower alkoxy or lower alkylthio; and $R^{39}$ represents lower alkyl or aralkyl, e.g. benzyl.

Other preferred compounds of formula Ia, Ib and Ic are such wherein $R^{22}$ is phenyl, cyclohexyl, benzyl, otolyl, m-tolyl, p-tolyl, but-3-enyl, 3-methylbut-3-enyl, 2-methylpropyl, 2-oxo-2-ethoxyethyl, 2-oxo-2-(N,N-dimethylamino)ethyl, carboxymethyl, 3-hydroxymethylbutyl, 2-cyanoethyl, cyclohexylmethyl, 3-chloro-3-methylbutyl, 2-(N,N-dimethylamino)-2-cyanoethyl, 2-chloroethyl, 2-iodoethyl, ethyl, 2-phenylethyl, 2-methoxyethyl, 2-benzyloxyethyl or 2-acetoxyethyl.

Other preferred compounds of formula Ia, Ib and Ic are such wherein $R'^{22}$ is hydrogen.

Other preferred compounds of formula Ia, Ib and Ic are such wherein the side chain in the 17 position (i.e. —$C(R^{20})(R'^{20})$—$CH(R^{22})(R'^{22})$) is in the β position.

Other preferred compounds of formula Ia, Ib and Ic are such wherein $R^2$ together with $R^3$ is an additional double bond and $R'^3$ is hydrogen.

Other preferred compounds of formula Ia, Ib and Ic are such wherein $R^1$ is hydrogen, halogen, methyl, hydroxy or oxo; $R^2$ is selected from the group comprising hydrogen, hydroxy, $C_1$–$C_3$ alkyl, vinyl, $C_1$–$C_3$ alkoxy and halogen, or $R^2$ designates, together with $R^3$, an additional bond between the carbon atoms at which $R^2$ and $R^3$ are placed; $R^3$ is selected from the group comprising hydrogen, hydroxy, optionally substituted alkoxy, acyloxy, sulphonyloxy, phosphonyloxy, oxo, halogen, $C_1$–$C_4$ alkyl and a group of the general formula =$NOR^{38}$ wherein $R^{38}$ is hydrogen or $C_1$–$C_3$ alkyl, or $R^3$ designates, together with $R^2$, an additional bond between the carbon atoms at which $R^2$ and $R^3$ are placed; wherein $R^4$ and $R^{4'}$, which are different or identical with the proviso that they are not both hydroxy, are selected from the group comprising hydrogen, halogen, hydroxy and branched or unbranched $C_1$–$C_6$ alkyl which may be substituted by halogen, hydroxy or cyano, or wherein $R^4$ and $R^{4'}$ together designate methylene or oxo or, together with the carbon atom to which they are bound, form a cyclopropane ring, a cyclopentane ring, or a cyclohexane ring; $R^5$ is hydrogen, halogen or hydroxy, or $R^5$ designates, together with $R^6$, an additional bond between the carbon atoms at which $R^5$ and $R^6$ are placed; $R^6$ is hydrogen, hydroxy, halogen or oxo, or $R^6$ designates, together with $R^5$ or $R^7$, an additional bond between the carbon atoms at which $R^6$ and $R^5$ or $R^7$ are placed; $R^7$ is selected from the group comprising hydrogen, methylene, hydroxy, methoxy, acetoxy, oxo, halogen, $C_1$–$C_4$ alkyl and a group of the general formula =NOR$^{36}$ wherein $R^{16}$ is hydrogen or $C_1$–$C_3$ alkyl, or $R^7$ designates, together with $R^6$ or $R^8$, an additional bond between the carbon atoms at which $R^7$ and $R^6$ or $R^8$ are placed; $R^8$ is hydrogen, hydroxy or halogen, or $R^8$ designates, together with $R^7$, $R^9$ or $R^{14}$, an additional bond between the carbon atoms at which $R^8$ and $R^7$, $R^9$ or $R^{14}$ are placed; $R^9$ is hydrogen, hydroxy or halogen, or $R^9$ designates, together with $R^8$ or $R^{11}$, an additional bond between the carbon atoms at which $R^9$ and $R^8$ or $R^{11}$ are placed; $R^{11}$ is selected from the group comprising hydrogen, methylene, hydroxy, methoxy, acetoxy, oxo, halogen, $C_1$–$C_4$ alkyl and a group of the general formula =NOR$^{37}$ wherein $R^{37}$ is hydrogen or $C_1$–$C_3$ alkyl, or $R^{11}$ designates, together with $R^9$ or $R^{12}$, an additional bond between the carbon atoms at which $R^{11}$ and $R^9$ or $R^{12}$ are placed; $R^{12}$ is selected from the group comprising hydrogen, halogen, $C_1$–$C_4$ alkyl, methylene, hydroxy, methoxy, acetoxy, oxo and a group of the general formula =NOR$^{33}$ wherein $R^{33}$ is hydrogen or $C_1$–$C_3$ alkyl, or $R^{12}$ designates, together with $R^{11}$, an additional bond between the carbon atoms at which $R^{11}$ and $R^{12}$ are placed; $R^4$ is hydrogen or hydroxy, or $R^{14}$ designates, together with $R^{15}$, an additional bond between the carbon atoms at which $R^{14}$ and $R^{15}$ are placed; $R^{15}$ is selected from the group comprising hydrogen, halogen, $C_1$–$C_4$ alkyl, methylene, hydroxy, methoxy, oxo and a group of the general formula =NOR$^{32}$ wherein $R^{32}$ is hydrogen or $C_1$–$C_3$ alkyl, or $R^{15}$ designates, together with $R^{14}$ an additional bond between the carbon atoms at which $R^{15}$ and $R^{14}$ are placed; $R^{16}$ is selected from the group comprising hydrogen, halogen, $C_1$–$C_3$ alkyl, methylene, hydroxy, methoxy, oxo and a group of the general formula =NOR$^{34}$ wherein $R^{34}$ is hydrogen or $C_1$–$C_3$ alkyl, or $R^{16}$ designates, together with $R^{17}$, an additional bond between the carbon atoms at which $R^{16}$ and $R^{17}$ are placed; $R^7$ is hydrogen or hydroxy, or $R^{17}$ designates, together with $R^{16}$, an additional bond between the carbon atoms at which $R^{17}$ and $R^{16}$ are placed; $R^{20}$ is selected from the group comprising hydrogen, $C_1$–$C_4$ alkyl and hydroxymethyl, or $R^{20}$ and $R^{20'}$ together designate methylene or oxo; $R^{20'}$ is hydrogen, halogen, alkyl or hydroxy, $R^{22'}$ is hydrogen, hydroxy or oxo; $R^{22}$ represents phenyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; benzyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; cyclohexyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; cyclohexylalkyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; alkyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; alkenyl optionally substituted by one or more of the following groups which substituents may be different or identical: hydroxy, alkoxy, halogen (chloro, bromo or iodo), amino, N-alkylamino, N,N-dialkylamino, cyano, carboxy or oxo; and esters thereof.

Other preferred-compounds of formula Ia, Ib and Ic are such wherein $R^1$, $R^2$, $R^{14}$, $R^5$, $R^{11}$, $R^{12}$, $R^{15}$, $R^{16}$, $R'^{20}$ and $R'^{22}$ is each hydrogen, $R^3$ is hydrogen, lower alkyl or perfluoro(lower alkyl), $R'^3$ is hydroxy, or $R^3$ designates, together with $R'^3$, oxo, $R^4$ is hydrogen or together with $R^5$ a methano bridge or together with $R^5$ an additional bond, $R^5$ is lower alkyl, cyano, hydroxymethyl, a carbaldehyde, an oxime derived from a carbaldehyde, a carboxylic acid, a primary or secondary amide derived from a carboxylic acid, an ester with a $C_1$–$C_6$-alcohol group or together with $R^4$ a methano bridge or together with $R^4$ an additional bond, $R^7$ is together with $R^8$ an additional bond or hydrogen, if $R^8$ and $R^9$ or $R^8$ and $R^{14}$ stand together for an additional bond, $R^8$ is together with $R^7$ or with $R^9$ or with $R^{14}$ an additional bond, $R^9$ is together with $R^8$ an additional bond or a hydrogen atom, if $R^7$ and $R^8$ or $R^8$ and $R^{14}$ stand together for an additional bond, $R^{14}$ is, together with $R^8$, an additional bond or a hydrogen atom, if $R^7$ and $R^8$ or $R^8$ and $R^9$ stand together for an additional bond, $R^{17}$ is hydrogen in the alpha position, $R^{19}$ is methyl in the beta position, $R^{20}$ is methyl in the alpha position, and $R^{22}$ is 3-methylbutyl; and ester, salt, active metabolite or prodrugs thereof.

Other preferred compounds of formula Ia, Ib and Ic are such wherein $R^5$ is a $C_1$–$C_3$-alkyl group, preferably a methyl group, a cyano group, a hydroxymethyl group or together with $R^4$ a methano bridge or together with $R^4$ an additional bond.

It is to be understood that the above preferred substituents can be combined in any way with each other.

Examples of interesting and preferred compounds of the general formula Ia, Ib and Ic are as follows:

(20R)-20-Methyl-21-phenyl-5α-pregna-8,14-dien-3β-ol; (20R)-20-methyl-21-(3-methyl phenyl)-5α-pregna-8,14-dien-3β-ol; (20R)-20-methyl-2 1-(3-hydroxyphenyl)-5α-pregna-8,14-dien-3β-ol; (20R)-20-methyl-21-(cyclopentyl)-5α-pregna-8,14-dien-3β-ol; 24-nor-cholest-8,14-dien-3β-ol; (20R)-20-methyl-21-(cyclohexyl)-5α-pregna-8,14-dien-3β-ol; (20R)-20-methyl-22-phenyl-5α-pregna-8,14-dien-3β-ol; 23,24-dinor-cholest-8, 14-dien-3β-ol; (20R)-20-methyl-21-(cyclobutyl)-5α-pregna-8,14-dien-3β-ol; 4,4-dimethyl-17β-((1R)-methyl-3-methyl-2-butenyl)androsta-8,14-dien-3-β-ol; (20R)-20-methyl-23-dimethylamino-5α-pregna-8,14-dien-3β-ol; 3β-hydroxy-5α-cyanochol-8-en-24-oic acid-N,N-dimethyl amide; 5β-methychol-8-en-3-on-24-oic acid-N,N-dimethyl amide; 3β-hydroxy-4,4-dimethyl-5α,14β-chola-8,15-dien-24-oic acid-N,N-dimethyl amide; 3β-hydroxy-5α-cyanocholest-8-en-24-one; 5β-methylchol-8-en-3,24-dione; 3β-hydroxy-4,4-dimethyl-5α,14β-cholesta-8,15-dien-24-one; 3β-hydroxy-5α-cyanochol-8-en-24-oic acid cyclohexyl ester; 5α-methylchol-8-en-3-on-24-oic acid cyclohexyl ester; 3β-hydroxy-4,4-dimethyl-5α,14β-chola-8,15-dien-24-oic acid cyclohexyl ester; 3β-hydroxy-5α-chola-8,14-dien-24-oic acid-N-(4-methylpiperazinyl)amide; 3β-hydroxychola-5,7-dien-24-oic acid-N-(4-methylpiperazinyl)amide; 3β-hydroxy-5α-cyanochol-8-en-24-oic acid-N-(4-methylpiperazinyl)amide; 5β-methylchol-8-en-3-on-24-oic acid-N-(4-methylpiperazinyl)amide; 3β-hydroxy-4,4-dimethyl-5α,14β-chola-8,15-dien-24-oic acid-N-(4-methylpiperazinyl)amide; (20R)-20-methyl-21-phenyl-5α-pregna-5,7-dien-3β-ol; (20R)-20-methyl-21-(3-methylphenyl)-5α-pregna-5,7-dien-3β-ol; (20R)-20-methyl-21-(3-hydroxyphenyl)-5α-pregna-5,7-dien-3β-ol; (20R)-20-methyl-21-(cyclopentyl)-5α-pregna-5,7-dien-3β-ol; 24-nor-cholest-5,7-dien-3β-ol; (20R)-20-methyl- 21-(cyclohexyl)-5α-pregna-5,7-dien-3β-ol; (20R)-20-methyl-22-phenyl-5α-pregna-5,7-dien-3β-ol; 23,24-dinor-cholest-5,7-dien-3β-ol; (20R)-20-methyl-21-(cyclobutyl)-5α-pregna-5,7-dien-3β-ol; 4,4-dimethyl-17β-((1R)-methyl-3-methyl-2-butenyl)androsta-5,7-dien-3β-ol; (20R)-20-methyl-23-dimethylamino-5α-pregna-5,7-dien-3β-ol; cholesta-5,7-dien-25-chloro-3β-ol; cholesta-5,7-dien-26-chloro-3-β-ol; cholesta-5,7-dien-26-ol; nor-24-cholesta-8,11-dien-3β-ol; cholesta-4,8-dien-3β-ol; cholesta-4,8-dien-3α-ol; cholesta-4,8(14)-dien-3β-ol; cholesta-4,8(14)-dien-3β-ol; 5-cyano-5α-cholest-7-en-3α-ol; 5-cyano-5α-cholest-7-en-3β-ol; 5-cyano-5β-cholest-7-en-3α-ol; 5-cyano-5α-cholest-8-en-3α-ol; 5-cyano-5α-cholest-8-en-3β-ol; 5-cyano-5β-cholest-7-en -3α-ol; 5-cyano-5β-cholest-8-en-3β-ol; 5-cyano-5α-cholest-8(14)-en-3α-ol; 5-cyano-5β0-cholest-8(14)-en-3β-ol; 5-cyano-5β-cholest-8(14)-en-3β-ol; 5-cyano-5β-cholest-8(14)-en-3β-ol; 3',4α-dihydrocyclopropa[4,5]-5β-cholest-7-en-3β-ol; 3',4β-dihydrocyclopropa[4,5]-5α-cholest-7-en-3α-ol; 3',4α-dihydrocyclopropa[4,5]-5β-cholest-8-en-3β-ol; 3',4β-dihydrocyclopropa[4,5]-5α-cholest-8-en-3α-ol; 3',4α-dihydrocyclopropa[4,5]-5β-cholest-8(14)-en-3β-ol; 3',4β-dihydrocyclopropa[4,5]-5α-cholest-8(14)-en-3α-ol; 5-(hydroxymethyl)-5α-cholest-7-en-3β-ol; 5-(hydroxymethyl)-5α-cholest-7-en-3α-ol; 5-(hydroxymethyl)-5α-cholest-8-en-3β-ol; 5-(hydroxymethyl)-5βcholest-8-en-3α-ol; 5-(hydroxymethyl)-5α-cholest-8(14)-en-3β-ol; 5-(hydroxymethyl)-5β-cholest-8(14)-en-3α-ol; 5-methyl-5β-cholest-8-en-3-one; 5-methyl-5 β-cholest-8-en-3βol; 5-methyl-5 β-cholest-8-en-3α-ol; 5-methyl-5β-cholest-8(14)-en-3-one; 5-methyl-5β-cholest-8(14)-en-3β-ol; 5-methyl-5β-cholest-8(14)-en-3α-ol; 3-(trifluoromethyl)cholest-4,7-dien-3β-ol; 3-(trifluoromethyl)cholesta-4,7-dien-3β-ol; 3α-(trifluoromethyl)cholesta-4,8-dien-3β-ol; 3β-(trifluoromethyl)cholesta-4,8-dien-3α-ol; 3α-(trifluoromethyl)cholesta-4,8(14)-dien-3β-ol; 3β-(trifluoromethyl)cholesta-4,8(14)-dien-3α-ol; 5-methyl-24-nor-5β-cholest-8(14)-en-3-one; (20R)-5,20-dimethyl-21-phenyl-5β-pregn-8(14)-en-3β-one; (20R)-21-cyclohexyl-5,20-dimethyl-5β-pregn-8(14)-en-3-one; 5-methyl-24-nor-5β-cholesta-8(14), 23-dien-3-one; 4,4-dimethyl-24-benzoylamido-5α-chola-8,14-dien-3β-ol; 3β-hydroxy-4,4-dimethyl-5α-chola-8,14-dien-24-oic acid N-phenylalanine amide; mono(3β-hydroxy-4,4-dimethyl-5α-chola-8,14-dien)-24 succinate; 3β-hydroxy-4,4-dimethyl-5α-chola-8,14-dien-24-oic acid (1-methyl-4-hydroxypiperidinyl) ester; 3β-hydroxy-4,4-dimethyl-5α-chola-8,14-dien-24-oic acid-N-(norleucine)amide; 3β-hydroxy-4,4-dimethyl-5α-chola-8,14-dien-24-oic acid-N-(arginine)amide; 3β-hydroxy-4,4-dimethyl-5α-chola-8,14-dien-24-oic acid-N-(glutamic acid)amide; 3β-hydroxy-4,4-dimethyl-5α-chola-8,14-dien-24-oic acid-N-(leucine)amide; 3phydroxy-4,4-dimethyl-5α-chola-8,14-dien-24-oic acid methyl ester; 3β-hydroxy-4,4-dimethylchola-5,7-dien-24-oic acid methyl ester; 3β-hydroxy-4,4-dimethyl-5α-chola-8,14-dien-24-oic acid ethyl ester; 3β-hydroxy-4,4-dimethyl-5α-chola-8,14-dien-24-oic acid; 3β-hydroxy-4,4-dimethyl-5α-chola-8,14-dien-24-oic acid cyclohexyl ester; 3β-hydroxy-4,4-dimethyl-5α-cholesta-8,14-dien-24-one; 3β-hydroxy-4,4,24-trimethyl-5α-chola-8,14-dien-24-one; 3β-hydroxy-4,4-dimethyl-24-phenyl-5α-chola-8,14-dien-24-one; 3β-hydroxy-4,4-di-methyl-24-(3-pentyl)-5α-chola-8,14-dien-24-one; 3β-hydroxy-4,4-dimethyl-5α-chola-8,14-dien-24-oic acid-N-phenyl amide; 3β-hydroxy-4,4-dimethyl-5α-chola-8,14-dien-24-oic acid amide; 4,4-dimethyl-24-phenylamino-5α-chola-8,14-dien-3β-ol; 4,4-dimethyl-24-amino-5α-chola-8,14-dien-3β-ol; 4,4-dimethyl-5β-chola-8,14-dien-3β,24-diol; 3β-hydroxy-4, 4-dimethyl -5α-chola-8,14-dien-24-aldehyde; 4,4-dimethyl-17α-((1R)-methyl-4-methyl-3-pentenyl)-androsta-8,14-dien-3α-ol; 4,4-dimethyl-5α-cholesta-14,16,24-triene-3β-ol; 4,4-dimethyl-17β-((1R)-methyl-3-methyl-2-butenyl)androsta-8,14-dien-3β-ol; (20R)-4,4,20-trimethyl-21-(4-methylphenyl)-5α-pregna-8,14-dien-3β-ol; (20R)-4,4,20-trimethyl-21-(2-methylphenyl)-5α-pregna-8,14-dien-3β-ol; (20R)-4,4, 20-trimethyl-21-(cyclohexyl)-5α-pregna-8,14-dien-3-β-ol; (20R)-4,4,20-trimethyl-21-(3-hydroxyphenyl)-5α-pregna-8,14-dien-3β-ol; (20R)-4,4,20-trimethyl-22-(cyclohexyl)-5α-pregna-8,14-dien-3β-ol; 24-nor-4,4-dimethyl-5α-cholest-8,14-dien-3β-ol; 27-nor-4,4-dimethyl-5α-cholest-8,14,25-trien-3β-ol; (20R)-4,4,20-trimethyl-21-(cyclobutyl)-5α-pregna-8,14-dien-3β-ol; (20R)-4,4,20-trinmethyl-21-(cyclopentyl)-5α-pregna-8,14-dien-3β-ol; 25-chloro-4,4-dimethyl-5α-cholesta-8,14-dien-3β-ol; 4,4-dimethyl-24-(N,N-dimethylamino)-24-cyano-5α-cholesta-8,14-dien-3βol; 4,4-dimethylcholest-8,14,25-trien-3β-ol; 4,4-dimethyl-17β-((1R)-methyl-4-iodobutyl)androsta-8,14-dien-3β-ol; 4,4-dimethyl-17β-((1R)-methylbutyl)androsta-8,14-dien-3βol; 4,4-dimrethyl-17β-((1R)-methyl-4-cyanobutyl)androsta-8,14-dien-3β-ol; 4,4-dimethyl-17β-((1R)-methyl-4-cyanobutyl)androsta-8,14-dien-3β-ol; 27-nor-3β-hydroxy-4,4-dimethyl-5α-cholesta-8,14-dien-26-oic acid benzyl ester; 3β-hydroxy-4,4-dimethyl-5α-chola-8,14-dien-24-oic acid-N-(methionine methyl ester)amide; 3β-hydroxy-4,4-dimethyl-5α-chola-8,14-dien-24-oic acid-N-(methionine) amide; 3β-hydroxy-4,4-dimethyl-5×-chola-8,14-dien-24-oic acid-N-(4-methylpiperazinyl)amide; 3β-hydroxy-4,4-dimethyl-5α-chola-8,14-dien-24-oic acid-N-tert-butylamide; 3β-hydroxy-4,4-dimethyl-5α-chola-8,14-dien-24-oic acid-N-(isonipecotic acid ethyl ester)amide; 3β-phydroxy-4,4-dimethyl-5α-chola-8,14-dien-24-oic acid-N-(isonipecotic acid)amide; 3β-hydroxy-4,4-dimethyl-5α-chola-8,14-dien-24-oic acid-N-(phenylalanine methyl ester)amide; 3β-hydroxy-4,4-dimethylchola-5,7-dien-24-oic acid; 3phydroxy-4,4-dimethylchola-5,7-dien-24-oic acid-N-dimethyl amide; 4,4-dimethyl-24-acetamido-5α-chola-8,14-dien-3β-ol; 4,4-dimethyl-24-acetoxy-5α-chola-8,14-dien-3β-ol; 4,4-dimethyl-24-methoxy-5α-chola-8,14-dien-3β-ol; 4,4-dimethyl-24-benzyloxy-5α-chola-8,14-dien-3β-ol; 3β-hydroxy-4,4-dimethyl-5α-chola-8,14-dien-24-oic acid benzyl ester; 26,27-diethyl-3β-phydroxy-4,4-dimethyl-5α-cholesta-8,14-dien-26,27-dioate; 3β-hydroxy4,4-dimethyl-5α-cholesta-8,14-dien-26,27-dioic acid; and 27-nor-3β-hydroxy-4,4-dimethyl-5α-cholesta-8,14-dien-26-oic acid.

Preferred compounds of formula Ia, Ib and Ic are such which when tested by the method described below for agonistic properties (example 71) shows a relative activity of at least 50, preferably at least 80, or when tested by the method described below for antagonistic properties (example 72) shows a $IC_{50}$ value below 10, preferably below 2.

Examples of other preferred compounds are such not being active at the oestrogen receptor, and preferably compounds not being active at other hormone receptors.

Further preferred embodiments are mentioned in the appended claims.

As used in the present description and claims, a lower alkyl group—when used alone or in combinations—may be a straight or branched alkyl group. Preferably, said alkyl group contains not more than 6 carbon atoms. Examples of preferred alkyl groups are methyl, ethyl, propyl, isopropyl, butyl, tert-butyl, pentyl and hexyl, more preferred methyl, ethyl, propyl, isopropyl, butyl and tert-butyl, still more preferred methyl and ethyl. In a preferred embodiment of this invention, the alkyl group contains not more than 4 carbon atoms, preferably not more than 3 carbon atoms.

As used in the present description and claims, alkoxy designates a straight or branched alkoxy group, preferably containing not more than 6 carbon atoms, preferably not more than 4 carbon atoms, most preferred not more than 3 carbon atoms. Examples of preferred alkoxy groups are methoxy, ethoxy and propoxy, more preferred methoxy and ethoxy.

As used in the present description and claims, N-alkylamino is an alkyl group connected to an amino group. Preferably, said alkyl group is a lower alkyl group as defined above. Preferred N-alkylamino groups are methylamino and ethylamino.

As used in the present description and claims, N,N-alkylamino is two alkyl group which are the same or different and which are connected to an amino group. Preferably, said alkyl group are lower alkyl groups as defined above. Preferred N,N-alkylamino groups are N,N-dimethylamino, N,N-diethylamino and N-methyl-N-ethylamino.

As used in the present description and claims, the expression alkenyl designates a straight or branched alkenyl group preferably containing not more than 6 carbon atoms, preferably not more than 3 carbon atoms.

As used in the present description and claims, the expression halogen preferably designates chloro, bromo or iodide. Another group of preferred halogens are fluoro and chloro, preferably fluoro.

As used in the present description and claims, the expression $C_3$–$C_6$ cycloalkyl designates a cycloalkyl group containing 3 through 6 carbon atoms in the ring. Preferred examples are cyclopropyl and cyclopentyl.

As used in the present description and claims, the expression acyloxy designates a monovalent substituent comprising an optionally substituted $C_{1-3}$-alkyl or phenyl group linked through a carbonyloxy group; such as e.g. acetoxy, propionyloxy, butyryloxy, isobutyryloxy, aliphatic dicarboxylic acids, nicotinic acid, isonicotinic acid, ethylcarbonic acid, phosphoric acid sulphonic acid, sulphamic acid, benzoic acid, acetic acid, propionic acid and other aliphatic monocarboxylic acids.

A "metabolite" of a compound of formula Ia, Ib or Ic is an active derivative of a compound of formula Ia, Ib or Ic which is produced when the compound of formula Ia, Ib or Ic is metabolised. Metabolites of compounds of formula Ia, Ib or Ic can be identified either by administration of a compound of formula Ia, Ib or Ic to a host and an analysis of blood samples from the host, or by incubation of a compound of formula Ia, Ib or Ic with hepatic cells in vitro and analysis of the incubant.

A "prodrug" is a compound that either is converted into a compound of formula Ia, Ib or Ic in vivo or which has the same active metabolites as a compound of formula Ia, Ib or Ic.

The compounds of formula Ia, Ib or Ic have a number of chiral centres in the molecule and thus exists in several isomeric forms. All these isomeric forms and mixtures thereof are within the scope of the invention.

The compounds of the general formula Ia, Ib and Ic can be prepared analogously with the preparation of known compounds. Hence, synthesis of the compounds of formula Ia, Ib and Ic can followed the well established synthetic pathways described in the comprehensive sterol and steroid literature. The following books can be used as the key source in the synthesis: L. F. Fieser & M. Fieser: Steroids: Reinhold Publishing Corporation, NY 1959; Rood's Chemistry of Carbon Compounds (editor. S. Coffrey): Elsevier Publishing Company, 1971; J. Fried and J. A. Edwards: Organic Reactions in Steroid Chemistry, Vol. I and II, Van Nostrand Reinhold Company, New York, 1972; and especially Dictionary of Steriods (editors: R. A. Hill; D. N. Kirk; H. L. J. Makin and G. M. Murphy): Chapmann & Hall. The last one contains an extensive list of citations to the original papers covering the period up to 1990. All these books including the last mentioned citations are incorporated by reference. In addition, information in all the above publications (including patent specifications) dealing with preparation of compounds similar with compounds of formula Ia, Ib and Ic is incorporated by reference.

Particularly, the compounds of the present invention may be synthesised according to the following general procedures:

Cholesta-5,8-dien-3-ol 1, which is synthesised as described in the literature [*J.Lip.Res.* 37, 1529, (1996)], can be oxidised in an Oppenauer reaction to give cholesta-4,8-dien-3-one 2 pivaloyloxy, valeryloxy, benzoyl and the like. Optionally said acyloxy group may contain a hydroxy and/or carboxy group.

As used in the present description and claims, a statement that, e.g., $R^1$ is oxo means that oxo (=O) is present in the 1 position and, consequently, there is no hydrogen atom in the 1 position. Analogous considerations apply for similar situations. In other instances, two symbols together may represent oxo, e.g., $R^3$ and $R^{\prime 3}$.

As used in the present description and claims, a statement that, e.g., $R^{12}$ is methylene means that methylene (=CH$_2$) is present in the 12 position and, consequently, there is no hydrogen atom in this position. Analogous considerations apply for similar situations. In other instances, two symbols together may represent methylene, e.g., $R^4$ and $R^{\prime 4}$.

As used in the present description and claims, a statement that alkoxy is optionally substituted ($R^3$) means that the alkoxy group is substituted with a convenient substituent such as hydroxy or carboxy.

As used in the present description and claims, the expressions "a primary or secondary amide derived from a carboxylic acid" used for the substituent $R^5$ is a group of the general formula —CONHR$^{40}$ wherein $R^{40}$ is hydrogen or lower alkyl.

As used in the present description and claims, the expressions "an ester with a $C_1$–$C_6$-alcohol group" used for the substituent $R^5$ is a group of the general formula —COOR$^{41}$ wherein $R^{41}$ is lower alkyl or aralkyl.

As used in the present description and claims, the expression arakyl designates alkyl substituted by an aryl group, e.g. benzyl.

Salts of compounds of formula Ia, Ib and Ic are preferably pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in *Journal of Pharmaceutical Science*, 66 (1977), 2 et seq.

Esters of compounds of formula Ia, Ib and Ic are formally derived by esterification of one or more hydroxylic groups of a compound of formula Ia, Ib or Ic, respectively, with an acid which can for example be selected from the group of acids comprising succinic acid and other (scheme 1). In this reaction, the sterol is treated with a ketone like acetone, quinone or cyclohexanone in the presence of aluminum isopropoxide or aluminum tert-butoxide [e.g. *J.Chem. Soc.Perkin I* 2667 (1994)]. The sterol can also be oxidised with pyridinium dichromate [vide *Synth.Commun.* 20 (1990), 1167]. The same oxidation reaction can be carried out with cholesta-5,8(14)-dien-3β-ol, which is also synthesised as described in the literature [*J.Lip.Res.* 37 (1996), 1529,] to give cholesta-5,8(14)-dien-3-one. For this ketone, a laborious synthesis is described in the literature [*Bull. Soc. Chim. Fr* 2037, (1971)]. Cholesta-4,7-dien-3-one is synthesised according to literature procedures [*Liebigs Ann.Chem.* 542 (1939), 218,] (in scheme 1, the series with the $\Delta^8$-double bond are shown as an example, analogous reactions have to be performed in the $\Delta^7$- and $\Delta^{8(14)}$-series).

In the following, only the syntheses in the $\Delta^8$-series are described. The derivatives in the $\Delta^7$ and $\Delta^{8(14)}$-series can be synthesised by a skilled artisan from the corresponding starting materials in the same way.

scheme 1:

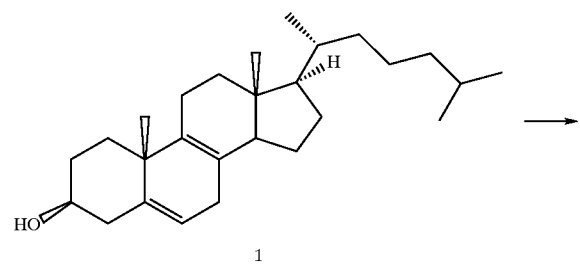

1

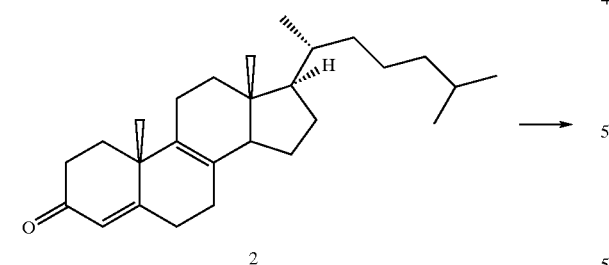

2

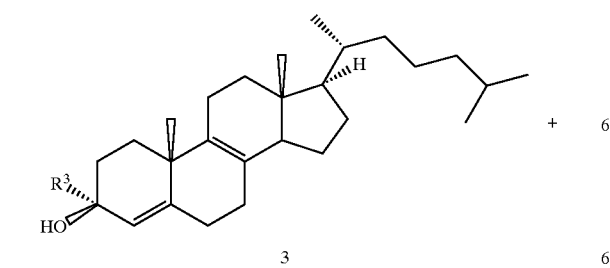

3

+

-continued

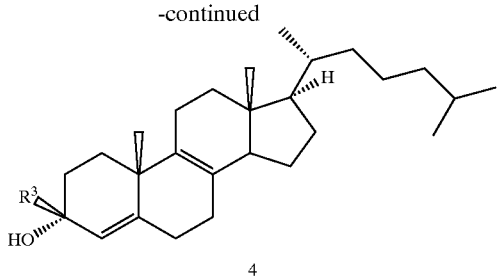

4

Enone 2 can be treated with different $C_1$–$C_6$-Grignard reagents to give two diastereomeric alcohols 3 and 4 (with $R^3$=$C_1$–$C_6$-alkyl), which are easily separated by column chromatography [e.g. *J.Med.Chem.* 40 (1997), 61].

Cholesta-4,8-dien-3-one 2 can be reduced according to well known literature procedures. Lithium aluminum hydride, sodium borohydride and diisobutylaluminum hydride are especially useful [e.g. *Liebigs Ann.Chem.* 542 (1939), 218]. Two diastereomeric alcohols of the formulae 3 and 4 (with R=hydrogen) can be obtained and readily separated by column chromatography.

For the introduction of perfluoroalkyl substituents in position 3, cholesta-4,8-dien-3-one 2 can be treated with perfluoroalkyltrialkylsilanes in the presence of fluoride sources like tetrabutyl-ammonium fluoride or caesium flouride. The trifluoromethyl group is preferentially introduced with reagents like trimethylsilyltrifluorornethane or triethylsilyltrifluoromethane [*J.Org.Chem.* 56 (1991), 984; *J.Org.Chem.* 54 (1989), 2873].

Again two diastereomeric alcohols of the formulae 3 and 4 (with $R^3$=perfluoroalkyl, preferentially: trifluoromethyl) can be obtained and readily separated by column chromatography.

The cyanoketones 5 and 6 are available starting from cholesta-4,8-dien-3-one 2 via a conjugate addition of cyanide (scheme 2). Different reagents like diethylaluminum cyanide [*J.Org.Chem.* 59 (1994), 2766] and some alkali and earth alkali metal cyanides [*Tetrahedron Lett.* 28 (1987), 4189; *Can.J.Chem.* 59 (1981), 1641] can be used in this reaction.

scheme 2:

2 →

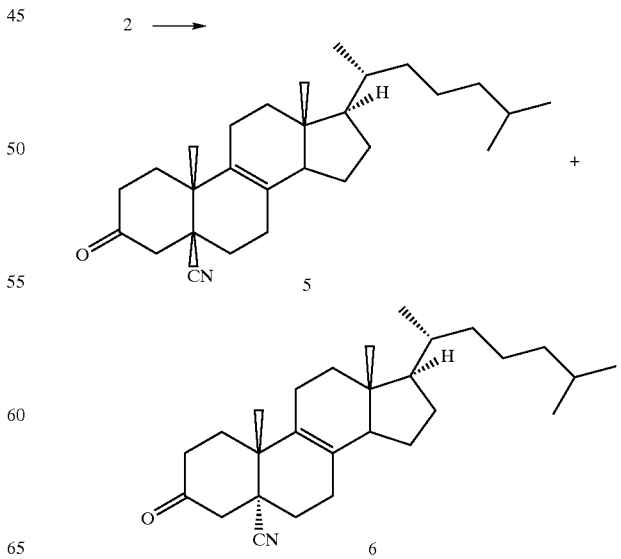

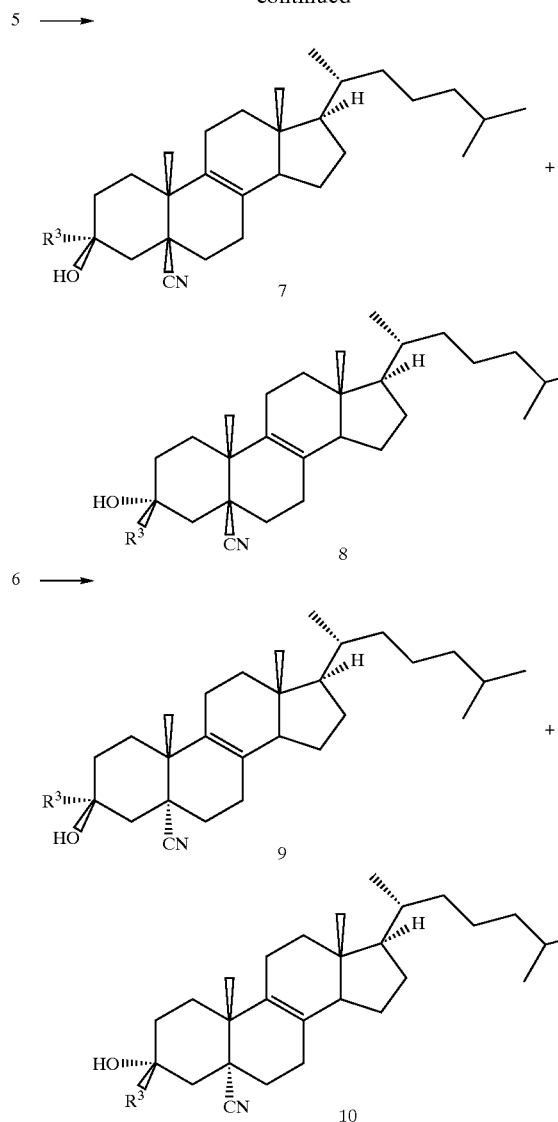

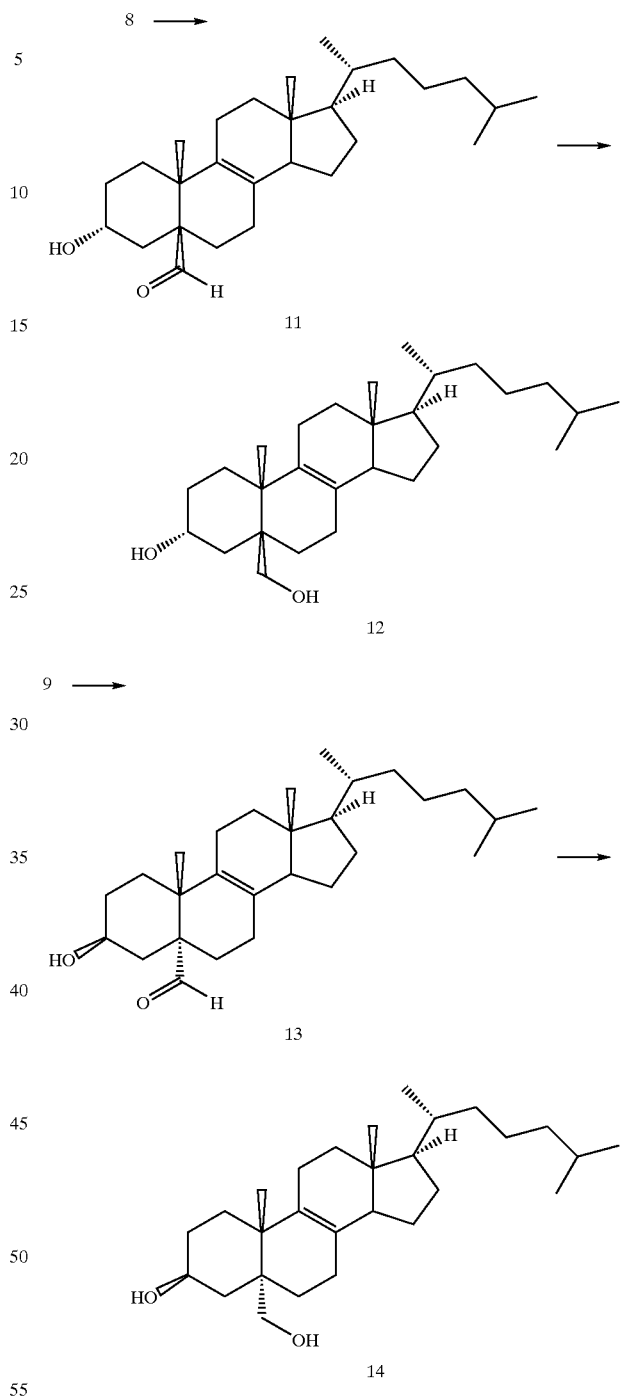

scheme 3:

The readily separated cyanoketones 5 and 6 can be reduced according to well known literature procedures. Lithium aluminum hydride, sodium borohydride and diisobutyl-aluminum hydride are used preferentially [e.g. Aust,J.Chem. 35 (1982), 629]. In the reduction reactions, two diastereomeric alcohols 7 and 8 ($R^3$=H), respectively, 9 and 10 ($R^3$=H) are obtained.

The cyanoketones of the formulae 5 and 6 can also be treated with Grignard reagents [e.g. Chem.Pharm.Bull. 9 (1961), 854] to give two diastereomeric tertiary alcohols 7 and 8 or 9 and 10 (with $R^3$=$C_1$–$C_6$-alkyl), respectively.

The hydroxymethyl derivatives of the formulae 12 and 14 can be synthesised in two step sequences from the cyanoalcohols 8 and 9, respectively (scheme 3). First the cyano group can be reduced with an electrophilic reducing agent like diisobutylaluminum hydride to give the corresponding imines, which are hydrolysed in situ to the carbaldehydes 11 and 13. In the second step, the carbaldehydes can be further reduced with well known reducing agents like lithium aluminum hydride, sodium borohydride or diisobutylaluminum hydride to the desired hydroxymethyl derivatives [e.g. J.Med.Chem. 39 (1996), 5092].

The methano derivatives of the formulae 15 and 16 can be synthesised form the allylic alcohols 3 and 4, respectively (scheme 4). Different variations of the Simmons-Smith reaction can be employed. As reagents, diiodomethane in the presence of zinc/copper-couple [e.g. J.Org.Chem. 31 (1966), 3869; J.Med.Chem. 39 (1996), 4218] as well as chloroiodomethane in the presence of a diethylzinc solution [J.Am.Chem.Soc. 108 (1986), 6343] can be used in this cyclopropanation reaction.

scheme 4:

3 ⟶

4 ⟶

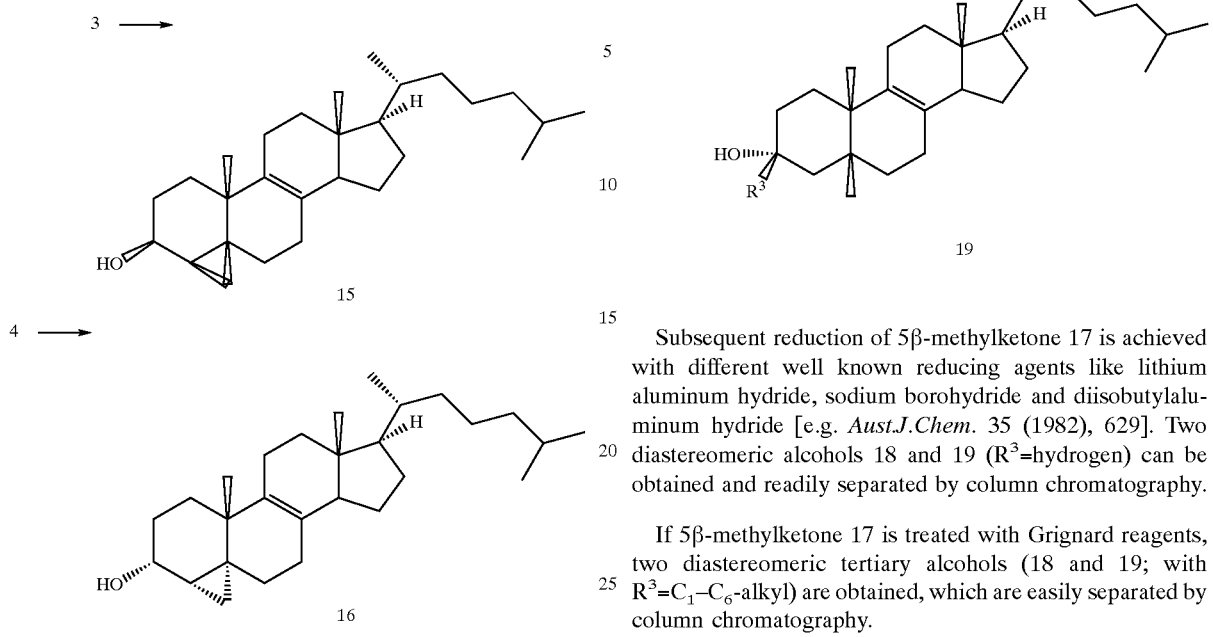

5β-Methylcholest-8-en-3-one 17 can be synthesised from cholesta4,8-dien-3-one 2 via a conjugate addition reaction (scheme 5). The methyl group is introduced either with lithium dimethylcuprate [e.g. Aust.J. Chem. 35 (1982), 629] or with methyl-Grignard compounds or trimethylaluminum in the presence of nickel catalysts [e.g. Tetrahedron Lett. 35 (1994), 6075; Synthesis 3 (1995), 317].

scheme 5:

2 ⟶

17 ⟶

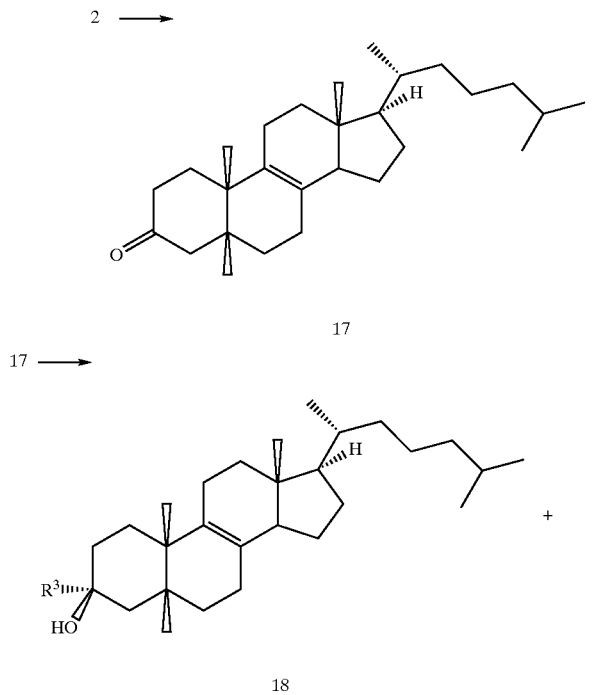

-continued

Subsequent reduction of 5β-methylketone 17 is achieved with different well known reducing agents like lithium aluminum hydride, sodium borohydride and diisobutylaluminum hydride [e.g. Aust.J.Chem. 35 (1982), 629]. Two diastereomeric alcohols 18 and 19 ($R^3$=hydrogen) can be obtained and readily separated by column chromatography.

If 5β-methylketone 17 is treated with Grignard reagents, two diastereomeric tertiary alcohols (18 and 19; with $R^3=C_1–C_6$-alkyl) are obtained, which are easily separated by column chromatography.

Analogues that combine a 5-cyano-substituent with different steroidal sidechains can be synthesized by the following general route (see scheme 6): Starting from lichesterol, which can be synthesized as described in the literature [J.Chem.Soc.Perkin Trans. 1 (1981), 2125], an enone can be generated by an oppenauer oxidation [e.g. J.Chem.Soc.Perkin Trans. 1 (1994), 2667]. A cyano group can be introduced by conjugate addition [J.Org.Chem. 59 (1994), 2766]. After protection of the 3-ketone as an ketal, the side chain can be cleaved by ozonolysis and subsequent reductive work up [Synthesis 3 (1990), 193]. The 22-alcohol can be transformed to the corresponding tosylate to generate the appropriate leaving group for the copper catalyzed addition of grignard reagents. By this addition, different alkyl- and aryl side chains can be intoduced [Chem.Pharm.Bull. 28 (1980), 606]. After deprotection of the ketone, the latter can be reduced to the corresponding α- and β-alcohols by standard methods.

Scheme 6:

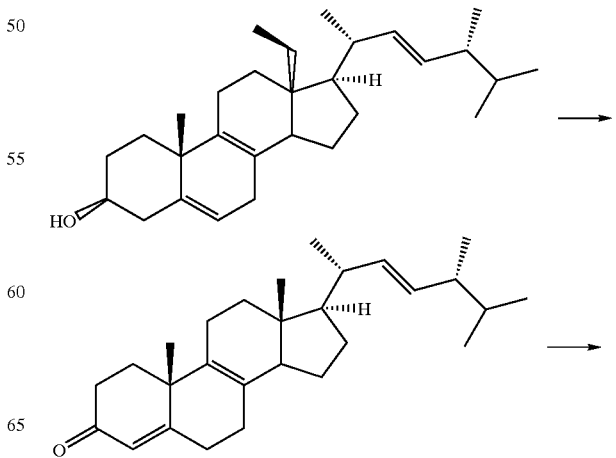

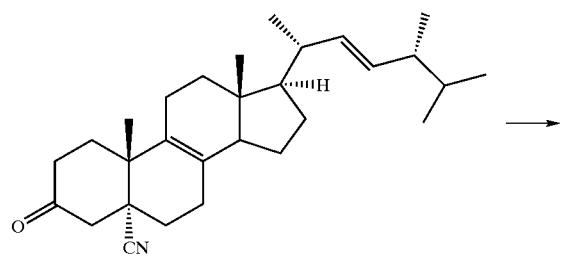

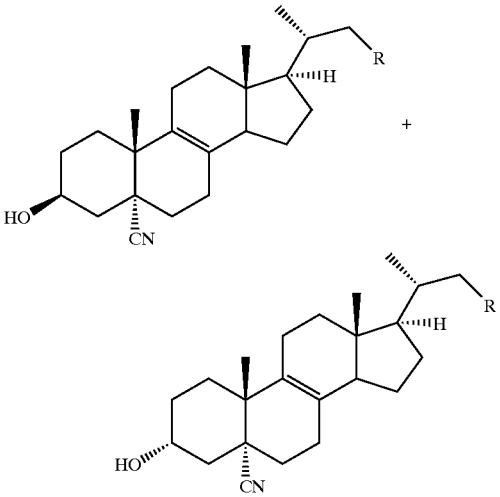

The compounds of the present invention will influence the meiosis in oocytes as well as in male germ cells.

The existence of a meiosis inducing substance in nature has been known for some time. However, until recently the identity of the meiosis inducing substance or substances was unknown.

The prospects of being able to influence the meiosis are several. According to a preferred embodiment of the present invention, a compound of formula Ia, Ib or Ic or an ester, salt, active metabolite or prodrug thereof can be used to stimulate the meiosis. According to another preferred embodiment of the present invention, a compound of formula Ia, Ib or Ic or an ester, salt; active metabolite or prodrug thereof can be used to stimulate themeiosis in humans. Thus, the compounds of formula Ia, Ib or Ic and ester, salt, active metabolite or prodrugs thereof are promising as new fertility regulating agents without the usual side effect on the somatic cells which are known from the hitherto used hormonal contraceptives which are based on estrogens and/or gestagens.

For use as a contraceptive agent in females, a meiosis inducing substance can be administered so as to prematurely induce resumption of meiosis in oocytes while they are still in the growing follicle, before the ovulatory peak of gonadotropins occurs. In women, the resumption of the meiosis can, for example, be induced a week after the preceding menstruation has ceased. When ovulated, the resulting overmature oocytes are then most likely not to be fertilised. The normal menstrual cycle is not likely to be affected. In this connection it is important to notice, that the biosynthesis of progesterone in cultured human granulosa cells (somatic cells of the follicle) is not affected by the presence of a meiosis inducing substance whereas the estrogens and gestagens used in the hitherto used hormonal contraceptives do have an adverse effect on the biosynthesis of progesterone.

According to another aspect of this invention, a meiosis inducing substance of formula Ia, Ib or Ic or an ester, salt, active metabolite or prodrug thereof can be used in the treatment of certain cases of infertility in females, including women, by administration thereof to females who, due to an insufficient own production of meiosis activating substance, are unable to produce mature oocytes. Also, when in vitro fertilisation is performed, better results can be achieved, when a compound of formula Ia, Ib or Ic or an ester, salt, active metabolite or prodrug thereof is added to the medium in which the oocytes are cultured.

When infertility in males, including men, is caused by an insufficient own production of the meiosis activating substance and thus a lack of mature sperm cells, administration of a compound of formula Ia, Ib or Ic or an ester, salt, active metabolite or prodrug thereof may relieve the problem.

As an alternative to the method described above, contraception in females can also be achieved by administration of a compound of formula Ia, Ib or Ic or an ester, salt, active metabolite or prodrug thereof which inhibits the meiosis, so that no mature oocytes are produced. Similarly, contraception in males can be achieved by administration of a compound of formula Ia, Ib or Ic or an ester, salt, active metabolite or prodrug thereof which inhibits the meiosis, so that no mature sperm cells are produced.

The route of administration of compositions containing a compound of formula Ia, Ib or Ic or an ester, salt, active metabolite or prodrug thereof may be any route which effectively transports the active compound to its site of action.

Thus, when the compounds of this invention are to be administered to a mammal, they are conveniently provided in the form of a pharmaceutical composition which comprises at least one compound of formula Ia, Ib or Ic or an ester, salt, active metabolite or prodrug thereof in connection with a pharmaceutically acceptable carrier. For oral use, such compositions are preferably in the form of capsules or tablets.

From the above it will be understood that administrative regimen called for will depend on the condition to be treated. Thus, when used in the treatment of infertility, the administration may have to take place once only, or for a limited period, e.g. until pregnancy is achieved. When used as a contraceptive, the compounds of formula Ia, Ib or Ic or ester, salt, active metabolite or prodrugs thereof will either have to be administered continuously or cyclically. When used as a contraceptive by females and not taken continuously, the timing of the administration relative to the ovulation will be important.

Pharmaceutical Compositions

Pharmaceutical compositions comprising a compound of formula Ia, Ib or Ic or an ester, salt, active metabolite or prodrug thereof may further comprise carriers, diluents, absorption enhancers, preservatives, buffers, agents for adjusting the osmotic pressure, tablet disintegrating agents and other ingredients which are conventionally used in the art. Examples of solid carriers are magnesium carbonate, magnesium stearate, dextrin, lactose, sugar, talc, gelatin, pectin, tragacanth, methyl cellulose, sodium carboxymethyl cellulose, low melting waxes and cocoa butter.

Liquid compositions include sterile solutions, suspensions and emulsions. Such liquid compositions may be suitable for injection or for use in connection with ex vivo and in vitro fertilisation. The liquid compositions may contain other ingredients which are conventionally used in the art, some of which are mentioned in the list above.

Further, a composition for transdermal administration of a compound of this invention may be provided in the form of a patch and a composition for nasal administration may be provided in the form of a nasal spray in liquid or powder form.

The dose of a compound of formula Ia, Ib or Ic to be used will be determined by a physician and will depend, inter alia, on the particular compound employed, on the route of administration and on the purpose of the use. In general, the compositions of the invention are prepared by intimately bringing into association the active compound with the liquid or solid auxiliary ingredients and then, if necessary, shaping the product into the desired formulation.

Usually, not more than 1000 mg, preferably not more than 100 mg, and in some preferred instances not more than 10 mg, of a compound of formula Ia, Ib or Ic is to be administered to mammals, e.g. to man, per day.

None of the compounds of formula Ia, Ib and Ic have shown to be toxic when administered to man in an amount of 1000 mg per day.

The compounds of formula Ia, Ib or Ic thereof can be synthesised by methods known per se.

The present invention is further illustrated by the following examples which, however, are not to be construed as limiting the scope of protection. The features disclosed in the foregoing description and in the following examples may, in any combination thereof, be material for realising the invention in diverse forms thereof.

EXAMPLE 1

3β-Hydroxy-4,4-dimethyl-5α-chola-8,14-dien-24-oic acid methyl ester 4,4-Dimethyl-3-oxochol-5-en-24-oic acid methyl ester (19.8 g) (G. Aranda et al., *Tetrahedron* 43 (1987), 4147) is reduced with sodium borohydride (9.9 g) in 1900 ml methanol at room temperature. The solution is stirred for 20 hours. After aqueous work-up, 3β-hydroxy-4,4-dimethylchol-5-en-24-oic acid methyl ester (19.2 g) is isolated. Melting point: 136–138° C. $^1$H-NMR (CDCl$_3$, 400 MHz): δ=5.55 (1H, m); 3.67 (3H, s); 3.23 (1H, m).

3β-Hydroxy-4,4-dimethylchol-5-en-24-oic acid methyl ester (19.1 g) is suspended in 390 ml of N,N-dimethylformamide (hereinafter designated DMF) and 39 g of imidazol and 34.6 g of tert-butyldimethylsilyl choride is added. The reaction mixture is stirred at 70° C. for 20 hours. After aqueous work-up, a crude product 23.9 g is isolated. Crystallization from tetrahydrofurane/methanol (hereinafter tetrahydrofurane and methanol are designated THF and MeOH, respectively) yields 3β-tert-butyldimethylsilyloxy-4,4-dimethyl-chol-5-en-24-oic acid methyl ester (19.55 g). Melting point: 144–146° C. $^1$H-NMR (CDCl$_3$, 300 MHz): δ=5.52 (1H, m); 3.66 (3H, s); 3.18 (1H, m); 0.89 (9H, s); 0.02 (6H, m).

3β-tert-Butyldimethylsilyloxy-4,4-dimethylchol-5-en-24-oic acid methyl ester (9.75 g) is dissolved in a warm mixture of 122 ml of benzene and 475 ml of n-hexane, 1,3-dibromo-5,5-dimethylhydantoin (3.95 g) is added and the mixture is refluxed for 15 minutes. After cooling (fast) and evaporating to dryness under reduced pressure, 475 ml of α-xylene and 21.7 ml of quinaldine is added and the mixture is refluxed for 1 hour. After aqueous work-up and trituration with methanol 3β-tert-butyldimethylsilyloxy-4,4-dimethylchola-5,7-dien-24-oic acid methyl ester (8.22 g) is isolated. Melting point: 116–124° C. $^1$H-NMR (CDCl$_3$, 300 MHz): δ=5.88 (1H, m); 5.52 (1H, m); 3.65 (3H, s); 3.32 (1H, m); 0.89 (9H, s); 0.04 (6H, m).

3β-tert-Butyldimethylsilyloxy-4,4-dimethylchola-5,7-dien-24-oic acid methyl ester (1.0 g) is suspended in a mixture of 25 ml methanol and 3.4 ml of concentrated hydrogen chloride acid and refluxed overnight. After evaporation to dryness under reduced pressure the remanens is triturated with methanol and thereafter recrystallized with methanol/water to give the title compound (0.47 g). Melting point: 156–157° C. $^1$H-NMR (CDCl$_3$, 400 MHz): δ=5.36 (1H, s) 3.67 (3H, s); 3.23 (1H, m). MS (abbreviation for mass spectroscopy): Calculated: 414.6. Found 414.3.

EXAMPLE 2

3β-Hydroxy-4,4-dimethylchola-5,7-dien-24-oic acid methyl ester

3β-tert-Butyldimethylsilyloxy-4,4-dimethylchola-5,7-dien-24-oic acid methyl ester (0.50 g) is dissolved in 5 ml of dry THF and 0.48 g of tetra-butylammoniumfluoride hydrate and 0.4 g of pulverised molecular sieve is added and the mixture is stirred for 4 days. After column chromatography and crystallization from methanol/water and methanol, the title compound (195 mg) is isolated. Melting point: 124–128° C. $^1$H-NMR (CDCl$_3$, 400 MHz): δ=5.91 (1H, m); 5.53 (1H, m); 3.67 (3H, s). 3.4 (1H, m). MS: Calculated: 414.6. Found 414.3.

EXAMPLE 3

3β-Hydroxy-4,4-dimethyl-5α-chola-8,14-dien-24-oic acid ethyl ester

3β-tert-Butyldimethylsilyloxy-4,4-dimethylchola-5,7-dien-24-oic acid methyl ester (4.0 g) is suspended in a mixture of 60 ml of 96% ethanol, 10.1 ml of benzene and 10.1 ml of concentrated hydrogen chloride acid and refluxed for 3.5 hours. After aqueous work-up and column chromatography followed by crystallization from ethanol the title compound (1.37 g) is isolated. Melting point: 122–124° C. $^1$H-NMR (CDCl$_3$, 300 MHz): δ=5.35 (1H, s); 4.13 (2H, q); 3.25 (1H, m). 1.25 (3H, t). MS: Calculated: 428.7. Found 428.3.

EXAMPLE 4

3β-Hydroxy-4,4-dimethyl-5α-chola-8,14-dien-24-oic acid

3-Hydroxy-4,4-dimethyl-5α-chola-8,14-dien-24-oic acid ethyl ester (1.9 g) is suspended in a mixture of 190 ml of 96% ethanol and 63 ml of 1M sodium hydroxide. The mixture is stirred for 3.5 h at room temperature. After aqueous work-up and crystallization from ethanol/water, the title compound (1.48 g) is isolated. $^1$H-NMR (CDCl$_3$, 400 MHz): δ=5.36 (1H, s); 3.22 (1H, m); 1.03 (3H, s). 1.01 (3H, s); 0.97 (3H, d); 0.83 (3H, s); 0.81 (3H, s). MS: Calculated: 400.6. Found 400.3.

EXAMPLE 5

3β-Hydroxy-4,4-dimethyl-5α-chola-8,14-dien-24-oic acid cyclohexyl ester

3β-Hydroxy-4,4-dimethyl-5α-chola-8,14-dien-24-oic acid (0.2 g) is suspended in 10 ml of cyclohexanol, 0.1 ml of boron trifluoride diethyl etherate is added and the mixture is stirred at 55–60° C. for 20 hours. After evaporation to dryness under reduced pressure, the remanens is purified by column chromatography and crystallized from methanol to give the title compound (49 mg). Melting point: 130–132° C. $^1$H-NMR (CDCl$_3$): δ=5.35 (1H, s); 4.75 (1H, m); 3.24 (1H, m). MS: Calculated: 482.8. Found 482.4.

EXAMPLE 6

3β-Hydroxy4,4-dimethyl-5α-cholesta-8,14-dien-24-one

3β-Hydroxy-4,4-dimethyl-5α-chola-8,14-dien-24-oic acid methyl ester (18.2 g) is suspended in 400 ml of DMF and 14.8 g of imidazol and 13.0 g of t-butyldimethylsilylchloride is added. The reaction is stirred at 65° C. for 20 hours. After aqueous work-up and crystallization from ether/methanol, 3β-tert-butyldimethylsilyloxy-4,4-dimethyl-5α-chola-8,14-dien-24-oic acid methyl ester (21 g) is obtained. Melting point: 124–125° C. $^1$H-NMR (CDCl$_3$, 400 MHz): δ=5.34 (1H, s); 3.68 (3H, s); 3.2 (1H, m); 0.9 (9H, s); 0.04 (6H, m).

3β-tert-Butyldimethylsilyloxy4,4-dimethyl-5α-chola-8,14-dien-24-oic acid methyl ester (12 g) is dissolved in a mixture of 500 ml THF and 400 ml ethanol. 60 ml 1M sodium hydroxide is added and the mixture is stirred for 20 hours. After aqueous work-up and crystallization from ethanol/water, 30-tert-butyldimethylsilyloxy-4,4-dimethyl-5α-chola-8,14-dien-24-oic acid (11.26 g) is obtained. Melting point: 181–184° C. $^1$H-NMR (CDCl$_3$, 300 MHz): δ=5.34 (1H, s); 3.19 (1H, m); 0.9 (9H, s); 0.04 (6H, m).

3β-tert-Butyldimethylsilyloxy-4,4-dimethyl-5α-chola-8,14-dien-24-oic acid (5.0 g) is dissolved in 250 ml of dry dichloromethane. After cooling to −15° C., 2.14 ml of N-methylmorpholine and 1.27 ml isobutylchloroformate is added and the mixture is stirred at −15° C. for 20 minutes, whereupon 0.98 g of N,O-dimethylhydroxy/amine, HCl is added and the mixture is stirred overnight and the temperature is slowly elevated to room temperature. After aqueous work-up, 3β-tert-butyldimethylsilyloxy-4,4-dimethyl-5α-chola-8,14-dien-24-oic acid-N-methoxy-N-methyl amide (5.37 g) is obtained. Melting point: 134–135° C. $^1$H-NMR (CDCl$_3$, 300 MHz): δ=5.35 (1H, s); 3.69 (3H, s); 3.2 (1H, m); 3.18 (3H, s); 0.9 (9H, s); 0.04 (6H, m).

3β-tert-Butyldimethylsilyloxy-4,4-dimethyl-5α-chola-8,14-dien-24-oic acid-N-methoxy-N-methyl amide (0.57 g) is dissolved in 10 ml of dry THF and added to a solution of 10 mmol isopropylmagnesium bromide in 10 ml THF, whereupon it was cooled on an ice-bath. The mixture is stirred for some h and left overnight at 5° C. After aqueous work-up, column chromatography and crystallization from methanol, 3β-tert-butyldimethylsilyloxy-4,4-dimethyl 5α-cholesta-8,14-dien-24-one (238 mg) is obtained, Melting point: 120–122° C. $^1$H-NMR (CDCl$_3$, 300 MHz): δ=5.35 (1H, s); 3.2 (1H, m); 2.61 (1H, m); 0.9 (9H, s); 0.04 (6H, m).

3β-tert-Butyldimethylsilyloxy-4,4-dimethyl-5α-cholesta-8,14-dien-24-one (0.1 g) is dissolved in 5 ml of ethanol, 0.2 ml of 6N hydrogen chloride is added and the mixture is stirred for 2 days. After aqueous work-up, column chromatography and crystallization from ethanol/-water, the title compound (64 mg) is obtained. $^1$H-NMR (CDCl$_3$, 400 MHz): δ=5.35 (1H, s); 8.24 (1H, m); 2.62 (1H, m). MS: Calculated: 426.7. Found 426.3.

EXAMPLE 7

3β-Hydroxy-4,4,24-trimethyl-5α-chola-8,14-dien-24-one

3β-tert-Butyldimethylsilyloxy-4,4-dimethyl-5archola-8,14-dien-24 oic acid-N-methoxy-N-methyl amide (0.57 g) is reacted with methylmagnesiumbromide and hydrolysed with ethanol/HCl following the procedure outlined in example 6 to give the title compound (0.20 g). Melting point: 183–185° C. $^1$H-NMR (CDCl$_3$, 300 MHz): δ=5.35 (1H, s); 3.24 (1H, m); 2.17 (3H, s). MS: Calculated: 398.6. Found 398.3.

EXAMPLE 8

3βH-ydroxy-4,4-dimethyl-24-phenyl-5α-chola-8,14-dien-24-one

3β-tert-Butyldimethylsilyloxy-4,4-dimethyl-5α-chola-8,14-dien-24 oic acid-N-methoxy-N-methyl amide (0.57 g) is reacted with phenylmagnesiumbromide and hydrolysed with ethanol/HCl following the procedure outlined in example 6 to give the title compound (0.31 g). Melting point: 196–199° C. $^1$H-NMR (CDCl$_3$, 300 MHz): δ=8.0–7.4 (5H, m); 5.35 (1H, s); 3.24 (1H, m); 3.0 (2H, m). MS: Calculated: 460.7. Found 460.3.

EXAMPLE 9

3β-Hydroxy-4,4-dimethyl-24-(3-pentyl)-5α-chola-8,14-dien-24-one

3β-tert-Butyldimethylsilyloxy-4,4-dimethyl-5α-chola-8,14-dien-24 oic acid-N-methoxy-N-methyl amide (0.57 g) is reacted with 3-pentylmagnesiumbromide and hydrolysed with ethanol/HCl following the procedure outlined in example 6 to give the title compound (13 mg). $^1$H-NMR (CDCl$_3$, 300 MHz): δ=5.35 (1H, s); 3.23 (1H, m). MS: Calculated: 454.7. Found: 454.3.

EXAMPLE 10

3β-Hydroxy-4,4-dimethyl-5α-chola-8,14-dien-24-oic acid-N-phenyl amide

3β-tert-Butyldimethylsilyloxy-4,4-dimethyl-5x-chola-8,14-dien-24 oic acid (0.50 g) is dissolved in 15 ml of dry dichloromethane. After cooling to –15° C., 0.188 ml of N-methylmorpholine and 0.153 ml of isobutylchloroformiate is added and the mixture is stirred at –15° C. for 20 minutes, whereupon 0.44 ml of aniline is added. The mixture is stirred overnight and the temperature is slowly elevated to room temperature. After aqueous work-up and crystallization from methanol, 3β-tert-butyldimethylsilyloxy4,4-dimethyl-5α-chola-8,14-dien-24-oic acid-N-phenyl amide (0.431 g) is obtained. $^1$H-NMR (CDCl$_3$,400 MHz): δ=7.53 (2H, d); 7.34 (2H, t); 7.17 (1H,s); 7.12 (1H,t); 5.35 (1H,s); 3.21 (1H,m); 0.9 (9H,s); 0.04 (6H, m).

3β-tert-Butyldimethylsilyloxy-4,4-dimethyl-5-chola-8,14-dien-24-oic acid-N-phenyl amide (50 mg) is dissolved in 5 ml of ethanol, 0.2 ml of 6N hydrogen chloride is added and the mixture is stirred at room temperature overnight. After aqueous work-up and crystallization from methanol the title compound is obtained. (36 mg). $^1$H-NMR (CDCl$_3$, 400 MHz): δ=7.53 (2H, d); 7.33 (2H, t); 7.18 (1H, s); 7.12 (1H, t ); 5.36 (1H, s); 3.26 (1H, m). MS: Calculated: 475.7. Found: 475.4.

EXAMPLE 11

3β-Hydroxy-4,4-dimethyl-5α-chola-8,14-dien-24-oic acid amide

3β-tert-Butyldimethylsilyloxy-4,4-dimethyl-5α-chola-8,14-dien-24 oic acid (1.0 g) is reacted with ammonia and hydrolysed with ethanol/HCl following the procedure outlined in example 10 to give the title compound (147 mg). Melting point: 233–235° C. $^1$H-NMR (CDCl$_3$, 400 MHz)): δ=5.36 (1H, s); 5.45–5.2 (2H, broad d); 3.25 (1H, m). MS: Calculated: 399.6. Found 399.3.

EXAMPLE 12

4,4-Dimethyl-24-phenylamino-5α-chola-8,14-dien-3β-ol

3β-tert-Butyldimethylsilyloxy-4,4-dimethyl-5α-chola-8,14-dien-24 oic acid (0.15 g) is reacted with aniline following the procedure outlined in example 10 and reduced with lithium aluminium hydride (0.15 g) in THF at room temperature. Aqueous work-up and crystallization from methanol gives 3β-tert-butyldimethylsilyloxy-4,4-dimethyl-24-phenylamino-5α-chola-8,14-dien (106 mg). $^1$H-NMR (CDCl$_3$, 300 MHz)): δ=7.17 (2H, t); 6.69 (1H, t); 6.6 (2H, d); 5.35 (1H, s); 3.6 (1H, s); 3.2 (1H, m); 3.09 (2H, m); 0.9 (9H, s); 0.04 (6H, m).

3β-tert-Butyldimethylsilyloxy-44-dimethyl-24-phenylamino-5α-chola-8,14-dien (100 mg) is hydrolysed with ethanol/HCl at 50° C. Aqueous work-up and crystallization from ethanol gives the title compound (53 mg). Melting point: 178–180° C. $^1$H-NMR (CDCl$_3$, 300 MHz)): δ=7.19 (2H, t); 6.7 (1H, t); 6.63 (2H, d); 5.36 (1H, s); 3.6 (1H, s); 3.26 (1H, m); 3.1 (2H, m). MS: Calcualted: 461.7. Found: 461.3.

EXAMPLE 13

4,4-Dimethyl-24-amino-5α-chola-8,14-dien-3β-ol

The compound is synthesised following the procedure outlined in example 12. $^1$H-NMR (DMSO-d$_6$, D$_2$O+HCl): δ=5.3 (1H, s); 3.03 (1H, m); 2.77 (2H, m). MS: Calculated: 385.6. Found: 385.3.

EXAMPLE 14

4,4-Dimethyl-5α-chola-8,14-dien-3β,24-diol 4,4-Dimethyl-3-oxochol-5-en-24-oic acid methyl ester (6.0 g) (G. Aranda et al., *Tetrahedron* 43 (1987), 4147) is reduced with lithium aluminium hydride (3.3 g) in THF (600 ml). After aqueous work-up and crystallization from diethyl ether, 4,4-dimethyl-5-ene-3β,24-diol (5,21 g) is obtained. Melting point: 201–202° C. $^1$H-NMR (CDCl$_3$, 400 MHz): δ=5.55 (1H, m); 3.61 (2H, m); 3.23 (1H, m). MS: Calculated: 388.6. Found: 388.4.

A mixture of 4,4-dimethylchol-5-ene-3β,24-diol (57 g), imidazole (125 g) and tert-butyldimethylsilyl chloride (110.5 g) in DMF is stirred at 70° C. for 20 hours. After aqueous work-up and crystallization from methanol, 3β,24-bis(tert-butyldimethylsilyloxy)-4,4-dimethylchol-5-ene (87.7 g) is obtained. Melting point: 161–1620C; $^1$H-NMR (CDCl$_3$, 400 MHz): δ=5.53 (1H, m); 3.58 (2H, m); 3.21 (1H, m); 0.9 (18H, m); 0.03 (12H, m).

3β,24-Bis(tert-butyldimethylsilyloxy)-4,4-dimethylchol-5-ene (44 g) is dissolved in a warm mixture of hexane (2 l) and benzene (540 ml). 1,3-Dibromo-5,5-dimethylhydantoin (15.32 g) is added and the mixture is refluxed for 20 min and then cooled rapidly to room temperature, and the insoluble material is removed by filtration. The filtrate is concentrated under reduced pressure and o-xylene (2 l) and quinaldine (84 ml) is added. The mixture is refluxed for 1 hour. After aqueous work-up and trituration with methanol, 3β,24-bis(tert-butyldimethylsilyloxy)-4,4-dimethylchola-5,7-diene (39 g) is isolated. Melting point: 98–106° C. $^1$H-NMR (CDCl$_3$, 400 MHz): δ=5.9 (1H, m); 5.54 (1H, m); 3.58 (2H, m); 3.35 (1H, m); 0.91 (18H, s); 0.05 (12H, m).

A mixture of 3β,24-bis(tert-butyldimethylsilyloxy)-4,4-dimethylchola-5,7-diene (18.8 g) in 99.9% ethanol (375 ml), benzene (55 ml) and concentrated hydrochloric acid (55 ml) is heated to reflux for 4 hours. After standing overnight at room temperature, the reaction mixture is concentrated under reduced pressure. Crystallization of the remanens from ethanol/water gives 8.44 g of the title compound. Melting point: 203–208° C. $^1$H-NMR (CDCl$_3$, 400 MHz): δ=5.36 (1H, s); 3.62 (2H, m); 3.23 (1H, m).

EXAMPLE 15

3β-Hydroxy-4,4-dimethyl-5α-chola-8,14-dien-24-aldehyde 4,4-Dimethyl-5α-chola-8,14-dien-3β,24-diol (0.21 g) is dissolved in benzene (21 ml). Tris(triph chloride (1.04 g) is added and the mixture is stirred at room temperature for 20 hours. Purification by column chromatography gives the title compound (129 mg). $^1$H-NMR (CDCl$_3$, 300 MHz): δ=9.79 (1H, s); 5.36 (1H, s); 1.05 (3H, s) 1.01 (3H, s); 0.95 (3H, d); 0.82 (3H, s); 0.80 (3H, s).

EXAMPLE 16

4,4-Dimethyl-17β-((1R)-methyl-4-methyl-3-pentenyl)androsta-8,14-dien-3β-ol $^1$H-NMR (CDCl$_3$, 400 MHz): δ=5.35 (1H, s); 5.18 (1H, t); 3.24 (1H, dd), 1.7 (3H, s); 1.6 (3H, s).

EXAMPLE 17

4,4-Dimethyl-5α-cholesta-14,16,24-triene-3β-ol $^1$H-NMR (CDCl$_3$, 400 MHz): δ=5.98 (1H, m); 5.8 (1H, m); 5.12 (1H, t), 3.24 (1H, m); 1.7 (3H, s); 1.58 (3H, s).

EXAMPLE 18

4,4-Dimethyl-17β((1R)-methyl-3-methyl-2-butenyl)androsta-8,14-dien-3β-ol $^1$H-NMR (CDCl$_3$, 400 MHz): δ=5.35 (1H, s); 4.93 (1H, d); 3.24 (1H, m), 1.69 (3H, s); 1.65 (3H, s).

EXAMPLE 19

(20R)-4,4,20-Trimethyl-21-phenyl-5α-pregna-8,14-dien-3β-ol

19 A: According to *Steroids* 26 (1975), p. 339–357, the 4,4-dimethylstigmasterole has been synthesised.

19 B: Ozonolysis of compound 19A at −70° C. by slowly introduction of O$_3$, and following reduction at −70° C. by sodium-bis-(2-methoxyethoxy) aluminium hydride and further reduction at a temperature about −30° C. with lithium aluminium hydride gave afforded 23-nor4,4-dimethyl-5α-cholest-5-en-3β,22-diol, which was diacetylated in pyridine with acetic acid anhydride. (1 B).

19 C: Compound 19B was isomerised by reflux in ethanol/6M hydrochloric acid giving 23-nor-4,4-dimethyl-5α-cholest-8,14-dien-3β,22-diol.

19 D: Compound 19C. was selectively C-22 tosylated by treatment of p-toluene sulfonyl chloride in pyridine by standing over night in room temperature. The compound was purified by colom chromathography and crystalised.

NMR: H ppm: 0.78 s CH$_3$; 0.82 s CH$_3$; 0.98 d CH$_3$; 1.02 s CH$_3$; 2.46s CH$_3$-aromat; 3.22 m H 3 a; 5.38 s H15; 7.33 d 2H; 7,78 d 2H.

This intermediate, 19D, is used in several of the following examples.

19 E: Compound 19D was reacted with phenylmagnesium bromide catalysed by Li$_2$CuCl$_4$ giving the title compound. (*Chem.Pharm.Bull.* 28 (1980), p. 606–611; Masuo Monsaki et al.).

NMR: H ppm: 0.82 d CH$_3$; 0.83 s CH$_3$; 1.02 s CH$_3$; 1.03 s CH$_3$; 2,55 m 1H; 2,91 dd 1H; 3.25 m 3 a H; 5.4 s 1H (15); 7.17 m 2H; 7.28 m 3H.

EXAMPLE 20

(20R)-4,4,20-Trimethyl-21-(3-methylphenyl)-5α-pregna-8,14-dien-3β-ol

According to example 19 (cormpound 19 D) was reacted with 3-methylphenyl magnesium bromide and LI$_2$CUCl$_4$ giving the title compound.

NMR: H ppm: 0.80 d CH$_3$; 0.82 2s 2CH$_3$; 1.0 2s 2CH$_3$; 2.33 s CH$_3$-aromat; 3.27 m H3 a 5.40 s 1H; 6.98 m 3H; 7.17 1H.

EXAMPLE 21

(20R)-4,4,20-Trimethyl-21-(4-methylphenyl)-5α-pregna-8,14-dien-3δ-ol

According to example 19 (compound 19 D) was reacted with 4-methylphenyl magnesium bromide and Li$_2$CuCl$_4$ giving the title compound.

NMR: H ppm: 0.84 s, 2d 3 CH$_3$; 1.04 2s 2CH$_3$; 2.33 s CH$_3$-aromat; 3.25 m H3 a; 5.40 s 1H; 7.05 m 4H.

EXAMPLE 22

(20R)-4,4,20-Trimethyl-21-(2-methylphenyl)-5α-pregna-8,14-dien-3β-ol

According to example 19 (compound 19 D) was reacted with 2-methylphenyl magnesium bromide and Li$_2$CuCl$_4$ giving the title compound. NMR: H ppm: 0.84 s+2d, 3 CH$_3$; 1.04 2s 2CH$_3$; 2.32s CH$_3$-aromat; 3.25 m H3 a; 5.40 s 1H; 7.10 m 4H;

EXAMPLE 23

(20R), 4,20-Trimethyl-21-(cyclohexyl)-5α-pregna-8,14-dien-3β-ol

According to example 19 (compound 19D) was reacted with cyclohexyl magnesium bromide and Li$_2$CuCl$_4$ giving the title compound.

NMR: H: mmp: 0.81 s CH$_3$; 0.82 s CH$_3$; 0.90 d CH$_3$; 1.03 s CH$_3$; 104 s CH$_3$; 3.24sH3a; 5.37 s H;

MS:424.4.

EXAMPLE 24

(20R)-4,4,20-Trimethyl-22-(phenyl)-5α-pregna-8,14-dien-3β-ol

According to example 19 (compound 19 D) was reacted with tolyl magnesium bromide and Li$_2$CuCl$_4$ giving the title compound.

NMR: H; ppm: 0.80 s CH$_3$; 0.82 s CH$_3$; 1.02s CH$_3$; 1.04 s CH.; 1.06 d CH$_3$; 3.25 m H3 a; 5.35 s H; 7.18 m 3H ; 7.27 m 2H.

EXAMPLE 25

(20R)-4,4,20-Trimethyl-21-(3-hydroxyphenyl)-5α-pregna-8,14-dien-3β-ol

According to example 19 (compound 19 D) was reacted with 3-trimethylsilyloxyphenyl magnesium bromide and Li$_2$CuCl$_4$ giving the title compound.

NMR: H; ppm: 0.80 d CH$_3$; 0.83 s CH$_3$; 0.84 s CH$_3$; 1.01 s CH$_3$; 1.03 s CH$_3$; 3.26 m H3 a; 5.40 s H; 6.66 m 2H; 6.76 m H; 7.16 m H. MS: 434.3.

EXAMPLE 26

(20R)-4,4,20-Trimethyl-22-(cyclohexyl)-5α-pregna-8,14-dien-3β-ol

According to example 19 (compound 19 D) was reacted with cyclohexylmethyl magnesium bromide and CuLi$_2$Cl$_4$ giving the title compound.

NMR: H ppm: 0.80 s CH$_3$; 0.83 s CH$_3$; 0.91 d CH$_3$; 3.24 m H3 a; 5.35 s H.

MS: 483.3.

EXAMPLE 27

24-Nor-4,4-dimethyl-5α-cholest-8,14-dien-3β-ol

According to example 19 (compound 19 D) was reacted with isobutyl magnesium bromide and CuLi$_2$Cl$_4$ giving the title compound. NMR: H; ppm: 0.8.0 s CH$_3$; 0.84 s CH$_3$; 0.86 d CH$_3$; 0.88 d CH$_3$; 0.91 d CH$_3$; 1.02 s CH$_3$; 1.04 s CH$_3$; 3.25 m H3 a; 5.35 s H.

EXAMPLE 28

27-Nor-4,4-dimethyl-5α-cholesta-8,14,25-trien-3β-ol

According to example 19 (compound 19 D) was reacted with cyclopropylmethyl magnesium bromide and Li$_2$CuCl$_4$ giving the title compound.

NMR: H; ppm:=0.82 s CH$_3$; 0.84 S CH$_3$; 0.95 d CH$_3$; 1.02 s CH$_3$; 1.04 s CH$_3$; 3.24H3 a; 4.97 dd 2H; 5.37 s 1H; 5.82 m 1H.

EXAMPLE 29

(20R)-4,4,20-Trimethyl-21-(cyclobutyl)-5o-pregna-8,14-dien-3βol

In the reaction of example 28 there was further isolated a compound which was identified as the title compound.

NMR: H; ppm; 0.80 s CH3; 0.84 s CH$_3$; 0.89 d CH$_3$; 1.01 s CH$_3$; 1.03 s CH$_3$; 3.25 m H3 a; 5.35 s 1H.

EXAMPLE 30

(20R)-4,4,20-Trimethyl-21-(cyclopentyl)-5x-pregna-8,14-dien-3β-ol

According to example 19 (compound 19 D) was reacted with cyclopentyl magnesium bromide and Li$_2$CuCl$_4$ giving the title compound.

NMR: H ; ppm; 0.80 s CH$_3$; 0.82 s CH$_3$; 0.94 d CH3, 1.01 s CH$_3$; 1.03 s CH$_3$; 3.25 m H3 a; 5.35 s H.

EXAMPLE 31

25-Chloro-4,4-dimethyl-5α-cholesta-8,14-dien-3β-ol

A mixture of 3β-(tert-butyldimethylsilyloxy)-4,4-dimethylcholesta-5,7,25-triene (50 mg), benzene (5 mL), ethanol (5 mL) and concentrated HCl (2 mL) was heated under reflux for 4 hours. The reaction was concentrated to half volume under reduced pressure and water (5 mL) was added. Extraction of the aqueous phase with dichloromethane and concentration under reduced pressure gave a residue, which was purified by flash chromatography. Recrystallisation from ethyl acetate:hexane gave the title compound as a white solid (35 mg).

Melting point 131–133° C.

The $^1$H-NMR spectrum (CDCl$_3$, d) showed characteristic signals at: 0.78 (s), 0.80 (s, 3H), 0.92 (d), 0.99 (s), 1.02 (s), 1.52 (s), 1.55 (s), 3.22 (dd), 5.33.

The mass spectrum showed characteristic peaks at: 446:3 (M$^+$).

EXAMPLE 32

4,4-Dimethyl-24-(N,N-dimethylamino)-24-cyano-5α-cholesta-8,14-dien-3β-ol

To a mixture of 3-β-hydroxy-4,4-dimethyl-5α-chola-8,14-dien-24-aldehyde (10 mg. 0.03 mmol), dimethylamine hydrochloride (18 mg), sodium acetate (16 mg) and molecular seives (100 mg) in methanol (2 mL) was added sodium cyanoborohydride (8 mg) and the reaction stirred for 1.5 hours. Dilute HCl (0.2 mL) was added, followed by sodium bicarboriate solution (0.3 mL) and the seives were removed by filtration. Concentration of the remaining solution gave a residue which was purified by flash chromatographyto give the title compound (5 mg).

The $^1$H-NMR spectrum (CDCl$_3$, d) showed characteristic signals at: 0.80 (s, 3H), 0.82 (s, 3H), 0.95 (d), 1.01.(s, 3H), 1.02 (s, 3H), 2.30 (s, 6H), 3.20 (dd, 1H), 3.39–3.49 (m, 1H), 5.32 (s, 1H). The $^{13}$C-NMR spectrum (CDCl$_3$, d) showed characteristic signals at: 151.3, 142.3, 123.2, 117.5, 117.4, 79.1. The mass spectrum showed characteristic peaks at: 438.4 (M$^+$).

EXAMPLE 33

4,4-Dimethylcholest-8,14,25-trien-3β-ol

Step 1

A solution of (25R)-4,4-dimethyl-5α-cholesta-8,14-diene-3β,26-diol (69 mg, 0.16 mmol), toluene sulphonyl chloride (45 mg, 2.4 mmol) and pyridine 1.5 ml was stirred for 6 h at ice bath temperature and 3 h at room temperature. Concentration under reduced pressure and purification by flash chromatography gave (25R)-(26-tosyloxy)-4,4-dimethyl-5α-cholesta-8,14-diene-3β-ol (61 mg).

The $^1$H-NMR spectrum (CDCl$_3$, d) showed characteristic signals at: 0.75 (s), 0.82 (s), 0.84 (s), 0.86 (s), 1.00 (s), 1.03 (s), 1.20 (s), 2.42 (s, 3H), 3.20–3.30 (m, 1H), 3.62–3.80 (m, 2H), 5.33 (s, 1H), 7.32 (d, 2H), 7.75 (d, 2H).

Step 2

(25R)-(26-Tosyloxy)-4,4-dimethyl-5α-cholesta-8,14-diene-3β-ol (61 mg), sodium iodide (150 mg and dimethylformamide (2 mL) was heated at 60° C. for 4 hours. Water was added and the aqueous layer extracted with dichloromethane, concentration under reduced pressure gave (25R)-26-iodo-4,4-dimethyl-5α-cholesta-8,14-dien-3β-ol, which was dissolved in chloroform (5 mL). 1,8-Diazabicyclo(5.4.0)undec-7-ene was added and the solution was heated to reflux for 5 h, concentrated under reduced pressure and purified by flash chromatography. Recrystallisation from methanol gave the title compound (5 mg).

The $^1$H-NMR spectrum (CDCl$_3$, d) showed characteristic signals at: 0.80 (s), 0.82 (s), 0.93 (d), 1.00 (s), 1.02 (s), 1.51 (s), 1.71 (s), 3.20–3.30 (m, 1H), 4.62 (d, 2H), 5.33

EXAMPLE 34

4,4-Dimethyl-17β-((1R)-methyl-4-chlorobutyl)androsta-8,14-dien-3β-ol

Step 1

A mixture of 4,4-dimethyl-5α-chola-8,14-diene-3β-24-diol (900 mg, 23 mmol), tosyl chloride (470 mg, 24 mmol) in pyridine (20 mL) was stirred 6 h at ice bath temperature, poured into water and extracted with diethyl ether. Drying over magnesium sulphate, concentration under reduced pressure and purification by flash chromatography gave 24-toluene-sulphonyloxy-4,4-dimethyl-5α-chola-8,14-diene-3-ol (1.1 g).

The $^1$H-NMR spectrum (CDCl$_3$, d) showed characteristic signals at: 0.79 (s, 3H), 0.83 (s, 3H), 0.90 (d, 3H), 1.01 (s, 3H), 1.02 (s, 3H), 2.42 (s, 3H), 3.21 (dd, 1H), 3.52 (m, 2H), 4.01 (t, 2H), 5.33 (s, 1H), 7.35 (d, 2H), 7.80 (d, 2H).

Step 2

A mixture of 24-toluenesulphonyloxy-4,4-dimethyl-5α-chola-8,14-diene-3-ol (45 mg, 0.8 mmol) and lithium chloride (0.6 mmol) in dimethylformamide (1.5 mL) under nitrogen was heated at 60° C. for 2 hours. The reaction was then poured into water and extracted with diethyl ether. Drying over magnesium sulphate, concentration under reduced pressure and purification by flash chromatography followed by recrystallised from methanol gave the title compound, 12 mg.

The $^1$H-NMR spectrum (CDCl$_3$, d) showed characteristic signals at: 0.80 (s, 3H), 0.82 (s, 3H), 0.97 (d, 3H), 1.02 (s, 3H), 1.04 (s, 3H), 3.25 (dd, 1H), 3.52 (m, 2H), 5.36 (s, 1H). The mass spectrum showed characteristic peaks at: 404.2 (M$^+$).

EXAMPLE 35

4,4-Dimethyl-172((1R)-methyl-4-iodobutyl)androsta-8,14-dien-3β-ol

A mixture of 24-toluenesulphonyloxy4,4-dimethyl-5α-chola-8,14-diene-3-ol (100 mg, 0.18 mmol) and sodium iodide (0.9 mmol) in dimethylformamide (2 mL) under nitrogen was heated at 60° C. for 3 hours. The reaction was then poured into water and extracted with diethyl ether. Drying over magnesium sulphate, concentration under reduced pressure and purification by flash chromatography followed by recrystallised from methanol gave the title compound (40 mg).

The $^1$H-NMR spectrum (CDCl$_3$, d) showed characteristic signals at: 0.80 (s, 3H), 0.82 (s, 3H), 0.95 (d, 3H), 1.01 (s, 3H), 1.02 (s, 3H), 3.10–3.31 (m, 2H), 5.35 (s, 1H). The mass spectrum showed characteristic peaks at: 496.1 (M$^+$).

EXAMPLE 36

4,4-Dimethyl-17β-((1R)-methylbutyl)androsta-8,14-dien-3β-ol

To a solution of 24-toluenesulphonyloxy-4,4-dimethyl-5α-chola-8,14-diene-3-ol (100 mg, 0.18 mmol) in diethyl ether (25 mL) was added lithium aluminium hydride (40 mg, 1.1 mmol) and the reaction was stirred 16 hours at room temperature. The reaction was then poured into water and extracted with diethyl ether. Drying over magnesium sulphate, concentration under reduced pressure and purification by flash chromatography gave the title compound (41 mg).

The $^1$H-NMR spectrum (CDCl$_3$, d) showed characteristic signals at: 0.80 (s, 3H), 0.82 (s, 3H), 0.87 (t, 3H) 0.95 (d, 3H), 1.00 (s, 3H), 1.02 (s, 3H), 3.20–3.31 (m, 1H), 5.35 (m, 1H). The $^{13}$C-NMR spectrum (CDCl$_3$, d) showed characteristic signals at: 79.1, 117.8 (C-15), 123.2 (C-14), 142.1 (C-9), 151.4 (C-8). The mass spectrum showed characteristic peaks at: 370.3 (M$^+$).

EXAMPLE 37

4,4-Dimethyl-17β-((1R)-methyl-4-cyanobutyl)androsta-8,14-dien-3β-ol

A mixture of 24-toluenesulphonylloxy-4,4-dimethyl-5α-chola-8,14-diene-3-ol (500 mg, 0.5 mmol) and sodium cyanide (90 mg, 2 mmol) in dimethylsulphoxide (2 mL) under nitrogen was heated at 140° C. for 2.5 hours. The reaction was then poured into ammonium chloride solution and extracted with dichloromethane. Drying over magnesium sulphate, concentration under reduced pressure and purification by flash chromatography gave the title compound (240 mg).

The $^1$H-NMR spectrum (CDCl$_3$, d) showed characteristic signals at: 0.81 (s, 3H), 0.83 (s, 3H), 0.97 (d, 3H), 1.00 (s, 3H), 1.02 (s, 3H), 3.18–3.31 (m, 1H), 5.35 (m, 1H). The mass spectrum showed characteristic peaks at: 395.3 (M$^+$).

EXAMPLE 38

27-Nor-3β-hydroxy-4,4-dimethyl-5α-cholesta-8,14-dien-26-oic acid benzyl ester

The compound is synthesised following the procedures outlined in example 52, below.

$^1$H-NMR (CDCl$_3$, 400 MHz): δ=7.35 (5H, m); 5.34 (1H, s); 5.11 (2H, s); 3.23 (1H, m).

EXAMPLE 39

3β-Hydroxy-4,4-dimethyl-5α-chola-8,14-dien-24-oic acid-N-(methionine methyl ester)amide 3β-Hydroxy4,4-dimethyl-5α-chola-8,14-dien-24-oic acid methyl ester (18.0 g) is suspended in 300 ml of DMF and 14.8 g of imidazol, and 13 g of tert-butyldimethylsilylchlocide is added. The reaction mixture is stirred at 70° C. for 20 hours. After aqueous work-up, and crystallisation from diethyl etherlmethanol, 21.0 g of 3β-tert-butyldimnethylsilyloxy-4,4-dimethyl-5α-chola-8,14-dien-24-oic acid methyl ester is isolated. Melting point, 124–125° C.

$^1$H-NMR (CDCl$_3$, 400 MHz): δ=5.34 (1H, s); 3.67 (3H, s); 3.19 (1H, m); 0.9 (9H, s); 0.03 (6H, m).

3β-tert-Butyldimethylsilyloxy-4,4-dimethyl-5α-chola-8,14-dien-24-oic acid methyl ester (3.6 g) is dissolved in a mixture of 150 ml of THF, 120 ml of ethanol and 18 ml of 1M sodium hydroxide. The mixture is stirred for 20 hours at room temperature and 2hours at 50° C. After aqueous work-up and crystallisation from ethanol/water, 2.48 g of 3β-tert-butyldimethylsilyloxy-4,4-dimethyl-5α-chola-8,14-dien-24-oic acid is isolated.

$^1$H-NMR (CDCl$_3$, 300 MHz): δ=5.33 (1H, s); 3.19 (1H, m); 0.9 (9H, s); 0.03 (6H, m).

3β-tert-Butyldimethylsilyloxy-4,4-dimethyl-5α-chola-8,14-dien-24-oic acid (0.5 9) is dissolved in 10 ml of dry dichloromethane and 0.213 ml of N-methylmorpholine. After cooling to −15° C. 0.132 ml of isobutylchloroformate is added and the mixture is stirred at −15° C. for 20 minutes, whereupon 0.232 g of L-methioninemethyl ester, hydrochloride is added and the mixture is stirred overnight and the temperature is slowly elevated to room temperature. After aqueous work-up, 3β-tert-butyldimethylsilyloxy-4,4-dimethyl-5α-chola-8,14-dien-24-oic acid-N-(methionine methyl ester)amide (0.60 g) is obtained.

$^1$H-NMR (CDCl$_3$, 300 MHz): δ=6.12 (1H, d); 5.34 (1H, s); 4.73 (1H, m); 3.76 (3H, s); 3.2 (1H, m); 2.1 (3H, s); 9.0 (9H, s); 0.03 (6H, m).

3β-tert-Butyldimethylsilyloxy-4,4-dimethyl-5α-chola-8,14-dien-24-oic acid-N-(methionine methyl ester) amide (0.20 g) is suspended in 20 ml methanol, and 0.1 ml 6M hydrogen chloride is added and the mixture is stirred at 50° C. for 1.5 hours and at room temperature for 20 hours. After crystallisation by adding of water, the title compound (165 mg) is obtained. Melting point: 138–141° C.

$^1$H-NMR (CDCl$_3$, 300 MHz): δ=6.12 (1H, d); 5.35 (1H, s); 4.73 (1H, m); 3.76 (3H, s); 3.23 (1H, m); 2.1 (3H, s). MS: Calculated: 545.8. Found 545.3.

EXAMPLE 40

3β-Hydroxy-4,4-dimethyl-5α-chola-8,14-dien-24-oic acid-N-(methionine)amide

3β-Hydroxy-4,4-dimethyl-5α-chola-8,14-dien-24-oic acid-N-(methionine methyl ester)amide (75 mg) is saponified overnight in a mixture of 10 ml of methanol, 5 ml of THF, 1 ml of water, and 0.6 ml of 1 M sodium hydroxide. After aqueous work-up and crystallisation from methanol, the title compound (56 mg) is obtained.

$^1$H-NMR (CDCl$_3$, 300 MHz): δ=6.35 (1H, d); 5.35 (1H, s); 4.7 (1H, m); 3.25 (1H, m); 2.12 (3H, s). MS: Calculated: 531.8. Found 531.8.

EXAMPLE 41

3β-Hydroxy-4,4-dimethyl-5α-chola-8,14-dien-24-oic acid-N-(4-methylpiperazinyl)amide 3β-tert-Butyldimethylsilyloxy-4,4-dimethyl-5α-chola-8,14-dien-24-oic acid (0.40 g) is reacted with N-methylpiperazine and hydrolysed with HCl/ethanol following the procedure outlined in example 39 to give the title compound (80 mg). Melting point: 189–191° C.

$^1$H-NMR (CDCl$_3$, 300 MHz): δ=5.35 (1H, s); 3.63 (2H, m); 3.48 (2H, m); 3.24 (1H, m); 2.31 (3H, s). MS: Calculated: 482.8. Found 482.3.

EXAMPLE 42

3β-Hydroxy-4,4-dimethyl-5α-chola-8,14-dien-24-oic acid-N-tert-butylamide

3β-tert-Butyldimethylsilyloxy-4,4-dimethyl-5α-chola-8,14-dien-24-oic acid (0.50 g) is reacted with tert-butylamine and hydrolysed with HCl/ethanol following the procedure outlined in example 39 to give the title compound (204 mg). Melting point: 171–176° C.

$^1$H-NMR (CDCl$_3$, 300 MHz): δ=5.35 (1H, s); 5.21 (1H, s); 3.24 (1H, m); 1.36 (9H, s). MS: Calculated: 455.7. Found 455.4.

EXAMPLE 43

3β-Hydroxy-4,4-dimethyl-5α-chola-8,14-dien-24-oic acid-N-(isonipecotic acid ethyl ester)amide 3β-tert-Butyldimethylsilyloxy-4,4-dimethyl-5α-chola-8,14-dien-24-oic acid (0.50 g) is reacted with ethylisonipecotate and hydrolysed with HCl/ethanol following the procedure outlined in example 39 to give the title compound (85 mg). Melting point: 116–119° C.

$^1$H-NMR (CDCl$_3$, 400 MHz): δ=5.35 (1H, s); 4.43 (1H, m); 4.15 (2H, q); 3.82 (1H, m); 3.25 (1H, m); 3.11 (1H, m); 2.8 (1H, m); 1.28 (3H, t). MS: Calculated: 539.8. Found 539.4.

EXAMPLE 44

3β-Hydroxy-4,4-dimethyl-5α-chola-8,14-dien-24-oic acid-N-(isonipecotic acid)amide 3β-Hydroxy-4,4-dimethyl-5α-chola-8,14-dien-24-oic acid-N-(isonipecotic acid ethyl ester)amide (36 mg) is saponified overnight in a mixture of 3 ml of ethanol and 0.2 ml of 1M sodiumhydroxide. After aqueous work-up and crystallisation from ethanol/water, the title compound (10 mg) is obtained. Melting point: 228–231° C.

$^1$H-NMR (CDCl$_3$, 400 MHz): δ=5.36 (1H, s); 4.45 (1H, m); 3.84 (1H, m); 3.27 (1H, m); 3.16 (1H, m); 2.86 (1H, m). MS: Calculated: 497.7. Found 497.6.

EXAMPLE 45

3β-Hydroxy-4,4-dimethyl-5α-chola-8,14-dien-24-oic acid-N-(phenylalanine methyl ester)amide 3β-tert-Butyldimethylsilyloxy-4,4-dimethyl-5α-chola-8,14-dien-24-oic acid (0.40 g) is reacted with phenylalanine methyl ester and hydrolysed with HCl/methanol following the procedures outlined in example 39 to give the title compound (86 mg). Melting point: 158–160° C.

$^1$H-NMR (CDCl$_3$, 400 MHz): δ=7.27 (3H, m); 7.09 (2H, m); 5.86 (1H, d); 5.35 (1H, s); 4.89 (1H, m); 3.73 (3H, s); 3.25 (1H, m); 3.13 (2H, m). MS: Calculated: 561.8. Found 561.5.

EXAMPLE 46

3β-Hydroxy-4,4-dimethylchola-5,7-dien-24-oic acid

3β-Hydroxy-4,4-dimethylchola-5,7-dien-24-oic acid methyl ester (120 mg) is saponified in a mixture of 15 ml of methanol, 15 ml of THF and 0.7 ml of 1M sodium hydroxide at 50° C. After aqueous work-up and crystallisation from methanol, the title compound (76 mg) is isolated. Melting point: 210–213° C.

$^1$H-NMR (CDCl$_3$, 400 MHz): δ=5.92 (1H, d); 5.55 (1H, m); 3.38 (1H, m). MS: Calculated: 400.6. Found 400.2.

EXAMPLE 47

3β-Hydroxy-4,4-dimethylchola-5,7-dien-24-oic acid-N-dimethyl amide

3β-tert-Butyldimethylsilyloxy-4,4-dimethylchola-5,7-dien-24-oic acid methyl ester (3.5 g) is saponified and reacted with dimethylamine following the procedure outlined in example 39. The tert-butyldimethylsilyl protecting group is split of by treatment with tetra-butylammoniumfluoride hydrate according to the procedure outlined in example 2 to give the title compound.

$^1$H-NMR (CDCl$_3$, 400 MHz) δ=5.92 (1H, d); 5.54 (1H, m); 3.4 (1H, m); 3.03 (3H, s); 2.96 (3H, s). MS: Calculated: 427.7. Found 427.4.

EXAMPLE 48

4,4-Dimethyl-24-acetamido-5α-chola-8,14-dien-3β-ol

3β-tert-Butyldimethylsilyloxy-4,4-dimethyl-5α-chola-8,14-dien-24-oic acid (5.0 g) is reacted with ammonia following the procedure outlined in example 39 and reduced with lithium aluminium hydride (3.0 g) in THF at room temperature. Aqueous work-up and crystallisation from methanol gives 2.6 g of 3β-tert-butyldimethylsilyloxy-4,4-dimethyl-24-amino-5α-chola-8,14-diene.

$^1$H-NMR (CDCl$_3$, 300 MHz): δ=5.34 (1H, s); 3.2 (1H, m); 3.0 (2H, broad s); 2.7 (1H, m); 0.9 (9H, s); 0.03 (6H, m). MS: Calculated: 499.9. Found 499.4.

3β-tert-Butyldimethylsilyloxy-4,4-dimethyl-24-amino-5α-chola-8,14-diene (0.50 g) is acetylated in a mixture of 20 ml of pyridine and 7 ml of acetic anhydride and hydrolysed with HCl/ethanol. After aqueous work-up and crystallisation from ethanol/water, the title compound (0.24 g) is isolated. Melting point: 219–221° C.

$^1$H-NMR (CDCl$_3$, 300 MHz): δ=5.43 (1H, s); 5.35 (1H, s); 3.23 (3H, m); 1.98 (3H, s). MS: Calculated: 427.7. Found 427.4.

EXAMPLE 49

4,4-Dimethyl-24-acetoxy-5α-chola-8,14-dien-3β-ol

3β-tert-Butyldimethylsilyloxy-4,4-dimethyl-5α-chola-8,14-dien-24-oic acid methyl ester (5.29 g) is reduced with lithium aluminium hydride (1.75 g) in 300 ml of THF at room temperature. After aqueous work-up and crystallisation from ethanol/water, 4.58 g of 3β-tert-butyldimethylsilyloxy-4,4-dimethyl-5α-chola-8,14-dien-24-ol is isolated.

$^1$H-NMR (CDCl$_3$, 400 MHz): δ=5.35 (1H, s); 3.65 (2H, m); 3.2 (1H, m); 0.9 (9H, s); 0.03 (6H, m).

3β-tert-Butyldimethylsilyloxy-4,4-dimethyl-5α-chola-8,14-dien-24-ol (150 mg) is acetylated in a mixture of 2 ml of pyridine and 1 ml of acetic anhydride. The tert-butyldimethylsilyl protecting group is split of by treatment with tetra-butylammonium fluoride hydrate according to the procedure outlined in example 2. After column chromatography and crystallisation from acetone/water, the title compound (36 mg) is obtained. $^1$H-NMR (CDCl$_3$, 300 MHz): δ=5.35 (1H, s); 4.05 (2H, m); 3.23 (1H, m); 2.04 (3H, s). MS: Calculated: 428.7. Found 428.3.

EXAMPLE 50

4,4-Di methyl-24-methoxy-5α-chola-8,14-dien-3β-ol

3β-tert-Butyldimethylsilyloxy-4,4-dimethyl-5α-chola-8,14-dien-24-ol (100 mg) is methylated with sodium hydride 60% (16 mg) and methyl iodine (0.125 ml) in 1 ml of DMF. The protecting tert-butyldimethylsilyl group is split of by treatment with HCl/ethanol. After aqueous work-up and crystallisation from methanol/water, the title compound (5 mg) is isolated.

$^1$H-NMR (CDCl$_3$, 300 MHz): δ=5.35 (1H, s); 3.36 (2H, m); 3.32 (3H, s); 3.23 (1H, m). MS: Calculated: 400.7. Found 400.3.

EXAMPLE 51

4,4-Dimethyl-24-benzyloxy-5α-chola-8,14-dien-3β-ol

The compound is synthesised following the procedure in example 50. Melting point: 114–115° C.

$^1$H-NMR (CDCl$_3$, 300 MHz): δ=7.38–7.23 (5H, m); 5.35 (1H, s); 4.51 (2H, s); 3.45 (2H, m), 3.24 (1H, m). MS: Calculated: 476.7. Found: 476.3.

EXAMPLE 52

3β-Hydroxy-4,4-dimethyl-5α-chola-8,14-dien-24-oic acid benzyl ester

3β-Hydroxy-4,4-dimethyl-5α-chola-8,14-dien-24-oic acid (100 mg) is suspended in 5 ml of dry DMF. 811 mg of cesium carbonate and 0.29 ml of benzyl chloride is added and the mixture is stirred at 50° C. overnight. After aqueous work-up, column chromatography and crystallisation from acetone/water 55 mg of the title compound is obtained. Melting point: 118–119° C.

$^1$H-NMR (CDCl$_3$, 300 MHz): δ=7.35 (5H, m); 5.35 (1H, s); 5.12 (2H, s); 3.23 (1H, m). MS: Calculated: 490.7. Found: 490.3.

EXAMPLE 53

26,27-Diethyl-3β-hydroxy-4,4-dimethyl-5α-cholesta-8,14-dien-26,27-dioate.

3β-tert-Butyldimethylsilyloxy-4,4-dimethyl-5α-chola-8,14-dien-24-ol (4.0 g) is dissolved in 80 ml of dry pyridine at 0° C. 3.04 g of p-toluenesulphonyl chloride is added and the mixture is stirred at 5° C. for 20 hours and at room temperature for 5 hours. After aqueous work-up and crystallisation from methanol, 3.01 g of 3β-tert-butyldimethylsilyloxy-4,4-dimethyl-24-p-toluenesulphonyloxy-5α-chola-8,14-diene is obtained.

$^1$H-NMR (CDCl$_3$, 300 MHz): δ=7.79 (2H, d); 7.34 (2H, d); 5.33 (1H, s); 4.02 (2H, m); 3.19 (1H, m); 2.43 (3H, s); 0.9 (9H, s); 0.03 (6H, m).

3β-tert-Butyldimethylsilyloxy-4-dimethyl-24-p-toluenesulphonyloxy-5α-chola-8,14-diene (0.50 g) is added to a mixture of 0.58 ml of diethyl malonate and 137 mg of sodium hydride (60%) in 10 ml of dry THF at −70° C. Stirring at −70° C. for 15 minutes, whereupon elevating of the temperature and reflux for 9 hours. After aqueous work-up and crystallisation from ethanol/water, 0.432 g of 26,27-diethyl-3β-tert-butyldimethylsilyloxy-4,4-dimethyl-5α-cholesta-8,14-dien-26,27-dioate is obtained.

$^1$H-NMR (CDCl$_3$, 300 MHz): δ=5.33 (1H, s); 4.21 (4H, q); 3.32 (1H, t); 3.2 (1H, m); 0.9 (9H, s); 0.03 (6H, m). MS: Calculated: 643.0. Found: 642.4.

26,27-Diethyl-3β-tert-butyldimethylsilyloxy-4,4-dimethyl-5α-cholesta-8,14-dien-26,27-dioate (0.41 g) is dissolved in 40 ml of ethanol and 0.5 ml of 6M hydrogen chloride. Stirring at room temperature for 48 h and 40° C. for 1 hour. The product is crystallised by adding of water and recrystallised from ethanol to give 141 mg of the title compound. Melting point: 105–106° C.

$^1$H-NMR (CDCl$_3$, 300 MHz): δ=5.35 (1H, s); 4.2 (4H, q); 3.33 (1H, t); 3.25 (1H, m); 1.25 (6H, t). MS: Calculated: 528.8. Found: 528.4

EXAMPLE 54

3β-Hydroxy-4,4-dimethyl-5α-cholesta-8,14-dien-26,27-dioic acid 26,27-Diethyl-3β-hydroxy-4,4-dimethyl-5α-cholesta-8,14-dien-26,27-dioate (95 mg) is saponified in a mixture of 5 ml of 96% ethanol, 5 ml of THF and 5 ml of 1M sodium hydroxide at room temperature. After aqueous work-up, the title compound is isolated (60 mg). Melting point: 188–190° C.

$^1$H-NMR (DMSO-d$_6$, 400 MHz): δ=12.63 (2H, s); 5.3 (1H, s); 4.37 (1H, s); 3.2 (1H, t); 3.03 (1H, m). MS: Calculated: 472.7. Found: 473.2 [M+H]$^+$.

EXAMPLE 55

27-Nor-3β-hydroxy-4,4-dimethyl-5α-cholesta-8,14-dien-26-oic acid

3β-Hydroxy-4,4-dimethyl-5α-cholesta-8,14-dien-26,27-dioic acid (535 mg) is suspended in 30 ml of o-xylene and refluxed overnight. After evaporation of o-xylene, the title compound is isolated by crystallisation from methanol/ether. Yield: 338 mg.

$^1$H-NMR (DMSO-d$_6$, 400 MHz): δ=11.95 (1H, s); 5.28 (1H, s); 4.35 (1H, m); 3.0 (1H, m). MS: Calculated: 428.7. Found: 428.2.

EXAMPLE 56

Synthesis of the intermediate cholesta-4,8-dien-3one

A solution of 2.20 9 cholesta-5,8-dien-3β-ol in 27 ml toluene and 6 ml cyclohexanone is refluxed for 10 minutes in a Dean-Stark apparatus. 0.57 g aluminum isopropoxide are added and the reaction mixture is refluxed for 30 minutes. After cooling and addition of sulfuric acid (2 N), the resulting mixture is extracted with ethyl acetate. The organic layer is separated, washed with saturated sodium bicarbonate solution and water, dried over anhydrous sodium sulphate and filtered. After evaporation of the solvent the residue is chromatographed with a mixture of hexane and ethyl acetate to give 1.53 g cholesta-4,8-dien-3-one as a white solid.

$^1$H-NMR (CDCl$_3$): δ=0.68 (s, 3H, H-18); 0.87 (2×d, J=7 Hz, 6H, H-26/27); 0.94 (d, J=7 Hz, 3H, H-21); 1.35 (s, 3H, H-19); 5.77 (s, 1H, H-4).

Cholesta-4,8(14)-dien-3-one is synthesised from cholesta-5,8(14)-dien-3β-ol in the same way. Cholesta-4,7-dien-3-one is synthesised according to literature procedures [*Just. Liebigs Ann.Chem.* 542(1939), 218,].

EXAMPLE 57 (SCHEME 1)

Cholesta-4,8-dien-3α-ol and cholesta-4,8-dien-3β-ol

To a solution of 520 mg cholesta-4,8-dien-3-one in 45 ml tetrahydrofuran 1.70 ml of a L-Selectride solution (1 N, in tetrahydofuran) are added dropwise at −75° C. The reaction mixture is warmed to room temperature within 4 hours, poured into hydrochloric acid (1 N) and extracted with ethyl acetate. The organic layer is separated, washed with brine, dried over anhydrous sodium sulphate and filtered. After evaporation of the solvent theresidue is chromatographed with a mixture of hexane and ethyl acetate to give 286 mg cholesta-4,8-dien-3β-ol and 20 mg cholesta-4,8-dien-3α-ol as white solids.

Cholesta-4,8-dien-3α-ol $^1$H-NMR (CDCl$_3$): δ=0.63 (s, 3H, H-18); 0.86 (2×d, J=7 Hz, 6H, H-26/27); 0.92 (d, J=7 Hz, 3H, H-21); 1.11 (s, 3H, H-19); 4.04 (m, 1H, H-3); 5.47 (d, H=5 Hz, 1H, H-4)

Cholesta-4,8-dien-3β-ol $^1$H-NMR (CDCl$_3$): δ=0.64 (s, 3H, H-18); 0.86 (2×d, J=7 Hz, 6H, H-26/27); 0.93 (d, J=7Hz, 3H, H-21); 1.23 (s, 3H, H-19); 2.47 (m, 1H); 4.19 (m, 1H, H-3); 5.32 (s, 1H, H-4)

Cholesta-4,7-dien-3α-ol and cholesta4,7-dien-3β-ol are synthesised according to literature procedures [*Just.Liebigs.Ann.Chem.* 542 (1939), 218].

EXAMPLE 58 (SCHEME 2)

a) 5-Cyano-5β-cholest-8-en-3-one and 5-cyano-5α-cholest-8-en-3-one 30 ml of a diethylaluminum cyanide solution (1 N, in toluene) are added to a solution of 3.82 g cholesta-4,8-dien-3-one in 60 ml tetrahydrofuran at 0° C. The reaction mixture is warmed to room temperature and stirred for 4 hours. 20 ml of a sodium hydroxide solution (1 N) are added before the mixture is extracted with diethyl ether. The organic layer is separated, dried over anhydrous sodium sulphate and filtered. After evaporation of the solvent the residue is chromatographed with a mixture of hexane and ethyl acetate to give 1.46 g 5-cyano-5β-cholest-8-en-3-one and 1.76 g 5-cyano-5α-cholest-8-en-3-one as pale yellow crystals.

5-Cyano-5β-cholest-8-en-3-one $^1$H-NMR (CDCl$_3$): δ=0.69 (s, 3H, H-18); 0.87 (2×d, J=7 Hz, 6H, H-26/27); 0.95 (d, J=7 Hz, 3H, H-21); 1.43 (s, 3H, H-19); 2.63 (m, 1H)

5-Cyano-5α-cholest-8-en-3-one $^1$H-NMR (CDCl$_3$): δ=0.64 (s, 3H, H-18); 0.87 (2×d, J=7 Hz, 6H, H-26/27); 0.95 (d, J=7 Hz, 3H, H-21); 1.37 (s, 3H, H-19); 2.52 (m, 2H)

5-Cyano-5β-cholest-7-en-3-one [which is known from the literature: *Aust.J.Chem.* 35 (1982), 629], 5-cyano-5α-cholest-7-en-3-one, 5-cyano-5β-cholest-8(14)-en-3-one and 5-cyano-5β-cholest-8(14)-en-3-one are synthesised from the corresponding starting materials in the same way.

b) 5-Cyano-5α-cholest-8-en-3β-ol and 5-cyano-5α-cholest-8-en-3α-ol 327 mg sodium borohydride are added to a solution of 1.76 g 5-cyano-5c-cholest-8-en-3-one in 200 ml ethanol at room temperature. The reaction mixture is stirred for 4 hours. After addition of hydrochloric acid (1 N) the resulting mixture is extracted with dichloromethane. The organic layer is separated, dried over anhydrous sodium sulphate and filtered. After evaporation of the solvent the residue is chromatographed with a mixture of hexane and ethyl acetate to give 0.36 mg 5-cyano-5α-cholest-8-en-3β-ol and 1.00 g 5-cyano-5α-cholest-8-en-3α-ol as white solids.

5-Cyano-5α-cholest-8-en-3β-ol $^1$H-NMR (CDCl$_3$): δ=0.59 (s, 3H, H-18); 0.86 (2×d, J=7 Hz, 6H, H-26/27); 0.92 (d, J=7 Hz, 3H, H-21); 1.08 (s, 3H, H-1 9); 4.12 (bm, 1H, H-3)

5-Cyano-5α-cholest-8-en-3α-ol $^1$H-NMR (CDCl$_3$): δ=0.63 (s, 3H, H-18); 0.89 (2×d, J=7 Hz, 6H, H-26/27); 0.94 (d, J=7 Hz, 3H, H-21); 1.06 (s, 3H, H-19); 4.11 (bm, 1H, H-3)

5-Cyano-5α-cholest-7-en-3β-ol, 5-cyano-5α-cholest-7-en-3α-ol, 5-cyano-5β-cholest-7-en-3α-ol, 5-cyano-5β-cholest-8-en-3β-ol, 5-cyano-5β-cholest-8-en-3α-ol, 5-cyano-5α-cholest-8(14)-en-3β-ol, 5-cyano-5α-cholest-8(14)-en-3α-ol, 5-cyano-5β-cholest-8(14)-en-3β-ol and 5-cyano-5β-cholest-8(14)-en-3α-ol are synthesised in the same way.

EXAMPLE 59 (SCHEME 3)

a) 3β-Hydroxy-5α-cholest-8-ene-5-carbaldehyde 4.66 ml of a diisobutylaluminum hydride solution (1.2 N, in toluene) are added to a solution of 230 mg 5-cyano-5α-cholest-8-en-3β-ol in 18 ml toluene at −10° C. The reaction mixture is stirred for 3 hours before 3.6 ml sulfuric acid (1 N) are added. After refluxing for one hour the resulting mixture is cooled to room temperature, diluted with water and extracted with dichloromethane. The organic layer is separated, dried over anhydrous sodium sulphate and filtered. After evaporation of the solvent 220 mg 3β-hydroxy-5α-cholest-8-ene-5-carbaldehyde are obtained as a white solid.

$^1$H-NMR (CDCl$_3$): δ=0.63 (s, 3H, H-18); 0.86 (2×d, J=7 Hz, 6H, H-26/27); 0.94 (d, J=7 Hz, 3H, H-21); 1.17 (s, 3H, H-19); 2.23 (m, 2H); 3.61 (m, 1H, H-3); 9.86 (s, 1 H, 5-CHO).

b) 5-(Hydroxymethyl)-5α-cholest-8-en-3β-ol

A suspension of 56 mg lithiumaluminum hydride in 5 ml tetrahydrofuran is added to a solution of 200 mg 3β-hydroxy-5α-cholest-8-en-5-carbaldehyde in 20 1964ml tetrahydrofuran at room temperature. After being heated to 50° C. for two hours the reaction mixture is cooled to room temperature. 0.06 ml water, 0.06 ml of a sodium hydroxide solution (1 N) and 0.18 ml water are added subsequently. The resulting suspension is stirred for 15 minutes and filtered over anhydrous sodium sulphate. After evaporation of the solvent the residue is crystallized from ethylacetate to give 80 mg 5-(hydroxymethyl)-5α-cholest-8-en-3β-ol as a white solid.

$^1$H-NMR (CDCl$_3$): δ=0.63 (s, 3H, H-18); 0.87 (2×d, J=7 Hz, 6H, H-26/27); 0.93 (d, J=7 Hz, 3H, H-21); 1.16 (s, 3H, H-19); 3.58 (s, 2H, 5-CH$_2$OH); 3.97 (m, 1H, H-3).

5-(Hydroxymethyl)-5α-cholest-7-en-3β-ol, 5-(hydroxymethyl)-5β cholest-8-en-3α-ol and 5-(hydroxymethyl)-5α-cholest-8(14)-en-3β-ol are synthesised in the same way.

EXAMPLE 60 (SCHEME 4)

3',4α-Dihydrocyclopropa[4,5]-5β-cholest-8-en-3β-ol 300 mg zinc dust and 0.03 ml glacial acetic acid are added to a solution 5.4 mg cupric acetate in 1.2 ml dimetoxyethane at room temperature. The mixture is stirred for 30 minutes before 0.01 ml triethylamine are added. After 5 minutes a solution of 100 mg cholesta-4,8-dien-3β-ol in 0.4 ml dimethoxyethane is added. Then 0.24 ml diiodomethane are added at such a rate that the reaction temperature does not rise above 40° C. The reaction mixture is stirred for further 6 hours. After addition of saturated ammonium chloride solution the resulting mixture is extracted with ethyl acetate. The organic layer is separated, washed with brine, dried over anhydrous sodium sulphate and filtered. After evaporation of the solvent the residue is chromatographed with a mixture of hexane and ethyl acetate to give 32 mg 3',4α-dihydrocyclopropa[4,5]-5β-cholest-8-en-3β-ol as a white solid.

$^1$H-NMR (CDCl$_3$): δ=0.25 (dd, J=9 Hz, 5 Hz, 1H, 4,5-CH$_2$); 0.63 (s, 3H, H-18); 0.76 (dd, J=5 Hz, 5 Hz, 1H, 4,5-CH$_2$); 0.87 (2×d, J=7 Hz, 6H, H-26/27); 0.94 (d, J=7 Hz, 3H, H-21); 1.11 (s, 3H, H-19); 4.32 (m, 1H, H-3).

EXAMPLE 61 (SCHEME 5)

a) 5-Methyl-5β-cholest-8-en-3-one 0.85 ml of a methyllithium solution (1.6 N, in diethyl ether) are added to a suspension of 130 mg cuprous iodide in diethyl ether at 0° C. The resulting mixture is stirred for one hour before a solution of 130 mg cholesta-4,8-dien-3-one in 1 ml diethyl ether is added. After being stirred for 30 minutes the reaction mixture is poured into saturated ammonium chloride solution and extracted with ethyl acetate. The organic layer is separated, washed with brine, dried over anhydrous sodium sulphate and filtered. After evaporation of the solvent the residue is chromatographed with mixture of hexane and ethyl acetate to give 80 mg-5-methyl-5, cholest-8-en-3-one as a white solid.

$^1$H-NMR (CDCl$_3$): δ=0.63 (s, 3H, H-18); 0.86 (2×d, J=-7 Hz, 6H, H-26/27); 0.90 (s, 3H, 5-CH$_3$); 0.93 (d, J=7 Hz, 3H, H-21); 1.06 (s, 3H, H-19); 2.42 (m, 1H)

b) 5-Methyl-5β-cholest-8-en-3α-ol and 5-methyl-5β-cholest-8-en-3β-ol 0.31 ml of a K-Selectride solution (1 N, in tetrahydrofuran) are added to a solution of 63 mg 5-methyl-5β-cholest-8-en-3-one in 4.4 ml tetrahydrofuran at −65° C. After being stirred for 2 hours the reaction mixture is allowed to warm to room temperature, poured into saturated ammonium chloride solution and extracted with ethyl acetate. The organic layer is separated, washed with brine, dried over anhydrous sodium sulphate and filtered. After evaporation of the solvent the residue is chromatographed with a mixture of dichloromethane and acetone to give 26 mg 5-methyl-5β-cholest-8-en-3α-ol and 21 mg 5-methyl-5β-cholest-8-en-3β-ol as white solids.

5-Methyl-5β-cholest-8-en-3α-ol $^1$H-NMR (CDCl$_3$): δ=0.59 (s, 3H, H-18); 0.85 (2×d, J=7 Hz, 6H, H-26/27); 0.86 (s, 3H); 0.90 (s, 3H); 0.92 (d, J=7 Hz, 3H, H-21); 3.82 (m, 1H, H-3).

5-Methyl-5β-cholest-8-en-3β-ol $^1$H-NMR (CDCl$_3$): δ=0.63 (s, 3H, H-18); 0.87 (2×d, J=7 Hz, 6H, H-26/27); 0.89 (s, 3H, 5-CH$_3$); 0.93 (d,-J=7 Hz, 3H, H-21); 0.99 (s, 3H, H-19); 3.87 (m, 1H, H-3)

5-Methyl-5β-cholest-8(14)-en-3-one, 5-methyl-5β-cholest-8(14)-en-3β-ol and 5-methyl-5β-cholest-8(14)-en-3α-ol are synthesised in the same way.

EXAMPLE 62 (SCHEME 1)

3β-(Trifluoromethyl)cholesta-4,8-dien-3α-ol and 3α-(trifluoromethyl)cholesta-4,8-dien-3β-ol.

0.2 ml triethylsilyltrifluoromethane and 328 mg tetrabutylarnmonium fluoride trihydrate are added to a solution of 200 mg cholesta-4,8-dien-3-one in 10 ml tetrahydrofuran at room temperature. After being stirred for 2 hours the reaction mixture is diluted with ethyl acetate, washed with water and brine, dried over anhydrous sodium sulphate and filtered. After evaporation of the solvent the residue is chromatographed with a mixture of hexane and ethyl acetate to give 45 mg 3β-(trifluoromethyl)cholesta-4,8-dien-3α-ol as a colourless oil and 170 mg 3α-(trifluormethyl)cholesta-4,8-dien-3β-ol as a white solid.

3β-(Trifluoromethyl)cholesta-4,8-dien-3α-ol $^1$H-NMR (CDCl$_3$): δ=0.65 (s, 3H, H-18); 0.87 (2×d, J=7 Hz, 6H, H-26/27); 0.93 (d, J=7 Hz, 3H, H-21); 1.18 (s, 3H, H-19); 2.41 (m, 1H,); 5.39 (s, 1H, H-4).

3α-(Trifluoromethyl)cholesta-4,8-dien-3β-ol $^1$H-NMR (CDCl$_3$): δ=0.64 (s, 3H, H-18); 0.87 (2×d, J=7 Hz, 6H, H-26/27); 0.93 (d, J=7 Hz, 3H, H-21); 1.25 (s, 3H, H-19); 2.43 (m, 1H,); 5.25 (s, 1H, H-4).

EXAMPLES 63+64

(20R)-5-Cyano-21-cyclohexyl-20-methyl-5α-pregn-8-en-3β-ol and (20R)-5-cyano-21-cyclohexyl-20-methyl-5α-pregn-8-en-3β-ol a) Ergosta-4,8,22-trien-3-one 1.90 g ergosta-5,8,22-trien-3β-ol (lichesterol) were treated with 0.50 g aluminum-tris-isopropylate as described in example 56. Column chromatography gave 1.54 g ergosta-4,8,22-trien-3-one as a white solid.

$^1$H-NMR (CDCl$_3$): δ=0.69 (s, 3H, H-18); 0.82–1.05 (4×d, 4× Me); 1.36 (s, 3H, H-19); 5.22 (m, 2H, H-22123); 5.77 (s, 1H, H-4)

b) 5-Cyano-5α-ergosta-8,22-dien-3-one 1.54 g ergosta-4,8,22-trien-3-one were treated with 11.73 ml diethylaluminum cyanide solution (1N, toluene) as described in example 58. After aqueous work up and chromatography 0.90 g 5-cyano-5α-ergosta-8,22-dien-3-one were isolated as a white solid (beside the corresponding 5β-cyano-compound).

¹H-NMR (CDCl₃): δ=0.66 (s, 3H, H-18); 0.82–1.05 (4×d, 4× Me); 1.28 (s, 3H, H-19); 5.21 (m, 2H, H-22/23)

c) 5-Cyano-3-(spiro-2',5'-dioxa-cyclopentyl)-5α-ergosta-8,22-diene

A mixture of 900 mg 5-cyano-5α-ergosta-8,22-dien-3-one, 0.97 ml ethylene glycol, 25 mg p-toluenesulfonic acid in 20 ml toluene was refluxed at a dean-stark-trap for 2 hours. After cooling, the reaction mixture was poured into saturated sodium bicarbonate solution, extracted with ethyl acetate and washed with water. The combined organic extracts were dried and evaporated to give 900 mg 5-cyano-3-(spiro-2',5'-dioxa-cyclopentyl)-5α-ergosta-8,22-diene as a white solid.

¹H-NMR (CDCl₃): δ=0.63 (s, 3H, H-18); 0.82–1.05 (4×d, 4×Me); 1.11 (s, 3H, H-19); 3.90–4.15 (m, 4H, 3-ketal); 5.20 (m, 2H, H-22/23).

d) (20R)-5-Cyano-3-(spiro-2', 5'-dioxa-cyclopentyl)-5α-pregn-8-ene-20-methanol 450 mg 5-cyano-3-(spiro-2',5'-dioxa-cyclopentyl)-5α-ergosta-8,22-diene were treated with ozone as described in example 19b. After reductive work up, 172 mg (20R)-5-cyano-3-(spiro-2',5'-dioxa-cyclopentyl)-5β-pregn-8-ene-20-methanol were isolated as a white solid.

¹H-NMR (CDCl₃): δ=0.65 (s, 3H, H-18); 1.06 (d, J=7 Hz, 3H, H-21); 1.1 (s, 3H, H-19); 3.35 (m, 1H, H-22); 3.66 (m, 1H, H-22); 3.90.4.12 (m, 4H, 3-ketal)

e) (20R)-5-Cyano-3-(spiro-2',5'-dioxa-cyclopentyl)-5α-pregn-8-ene-20-methanol-4-methylbenzene sulfonate 1.13 g (20R)-5-cyano-5α-pregn-8-ene-20-methanol was treated with 869 mg p-toluenesulfonyl chloride as described in example 19 d. After aqueous work up and column chromatography, 1.19 g (20R)-5-cyano-3-(spiro-2',5'-dioxa-cyclopentyl)-5α-pregn-8-ene-20-methanol-4-methylbenzene sulfonate were isolated.

¹H-NMR (CDCl₃): δ=0.59 (s, 3H, H-18); 1.00 (d, J=7 Hz, 3H, H-21); 1.10 (s, 3H, H-19); 3.70–4.12 [m, 4H (3-ketal)+2H (H-22)].

f) (20R)-5-Cyano-21-cyclohexyl-20-methyl-3-(spiro-2',5'-dioxa-cyclopentyl)-5α-pregn-8-ene 258 mg (20R)-5-cyano-3-(spiro-2',5'-dioxa-cyclopentyl)-5α-pregn-8-ene-20-methanol4-methylbenzene sulfonate were treated with cyclohexyl magnesium bromide analoguously to example 19e. After column chromatography, 147 mg (20R)-5-cyano-21-cyclohexyl-20-methyl-3-(spiro-2',5'-dioxa-cyclopentyl)-5α-pregn-8-ene were isolated as a pale yellow solid.

¹H-NMR (CDCl₃): δ=0.62 (s, 3H, H-18); 0.90 (d, J-7 Hz, 3H, H-21); 1.10 (s, 3H, H-19); 3.90–4.12 (m, 4H, 3-ketal)

g) (20R)-5-Cyano-21-cyclohexyl-20-methyl-5α-pregn-8-en-3-one

A mixture of 128 mg (20R)-5-cyano-21-cyclohexyl-20-methyl-3-(spiro-2',5'-dioxacyclopentyl)-5α-pregn-8-ene, 31 mg amberlyste 15 and 8 ml acetone was stirred at room temperature for 20 hours. After filtration and evaporation of the solvent 94 mg (20R)-5-cyano-21-cyclohexyl-20-methyl-5α-pregn-8-en-3-one were isolated.

¹H-NMR (CDCl₃): δ=0.67 (s, 3H, H-18); 0.90 (d, J=7 Hz, 3H, H-21); 1.27 (s, 3H, H-19); 2.55 (pseudo-s, 2H)

h) (20R)-5-Cyano-21-cyclohexyl-20-methyl-5α-pregn-8-en-3β-ol and (20R)-5-cyano-21-cyclohexyl-20-methyl-5α-pregn-8-en-3α-ol 90 mg (20R)-5-cyano-21-cyclohexyl-20-methyl-5α-pregn-8-en-3-one were treated with 33 mg sodium borohydride as described in example 58b. After column chromatography, 15 mg (20R)-5-cyano-21-cyclohexyl-20-methyl-5α-pregn-8-en-3β-ol and 25 mg (20R)-5-cyano-21-cyclohexyl-20-methyl-5α-pregn-8-en-3α-ol were isolated.

(20R)-5-cyano-21-cyclohexyl-20-methyl-5α-pregn-8-en-3β-ol

¹H-NMR (CDCl₃): δ=0.63 (s, 3H, H-18); 0.93 (d, J=7 Hz, 3H, H-21); 1.11 (s, 3H, H-19); 4.12 (broad-m, 1H, H-3)

(20R)-5-cyano-21-cyclohexyl-20-methyl-5α-pregn-8-en-3α-ol

¹H-NMR (CDCl₃): δ=0.62 (s, 3H, H-18); 0.92 (d, J=7 Hz, 3H, H-21); 1.06 (s, 3H, H-19); 4.12 (narrow-m, 1H, H-3)

EXAMPLES 65+66

(20R)-5-Cyano-21-phenyl-20-methyl-5α-pregn-8-en-3β-ol and (20R)-5-cyano-21-phenyl-20-methyl-5α-pregn-8-en-3α-ol a) (20R)-5-Cyano-21-phenyl-20-methyl-3-(spiro-2', 5'-dioxa-cyclopentyl)-5α-pregn-8-ene 400 mg (20R)-5-cyano-3-(spiro-2',5'-dioxa-cyclo pentyl)-5α-pregn-8-ene-20-methanol-4-methylbenzene sulfonate (example 63e) were treated with phenyl magnesium bromide analoguously to example 63f. After column chromatography, 190 mg (20R)-5-cyano-21-phenyl-20-methyl-3-(spiro-2',5'-dioxa-cyclopentyl)-5α-pregn-8-ene were isolated as a white solid.

¹H-NMR (CDCl₃): δ=0.65 (s, 3H, H-18); 0.84 (d, J=7 Hz, 3H, H-21); 1.12 (s, 3H, H-19); 2.90 (dd, J=12 hz, J=3 Hz, 1H, H-21); 3.90–4.12 (m, 4H, 3-ketal); 7.12–7.3 b) (20R)-5-Cyano-21-phenyl-20-methyl-5α-pregn-8-en-3-one 180 mg (20R)-5-cyano-21-phenyl-20-methyl-3-(spiro-2',5'-dioxa-cyclopentyl)-5α-pregn-8-ene were treated with amberlyste 15 as described in example 63g. After filtration and evaporation of the solvent, 164 mg (20R)-5-cyano-21-phenyl-20-methyl-5α-pregn-8-en-3-one were isolated.

¹H-NMR (CDCl₃): δ=0.68 (s, 3H, H-18); 0.84 (d, J=7 Hz, 3H, H-21); 1.27 (s, 3H, H-19); 2.55 (pseudo-s, 2H); 2.90 (dd, J=12 hz, J=3 Hz, 1H, H-21); 7.12–7.30 (m, 5H, pH)

c) (20R)-5-Cyano-21-phenyl-20-methyl-5α-pregn-8-en-3β-ol and (20R)-5-cyano-21-phenyl-20-methyl-5α-pregn-8-en-3α-ol 152 mg (20R)-5-cyano-21-cyclohexyl-20-methyl-5α-pregn-8-en-3-one were treated with 50 mg sodium borohydride as described in example 58b. After column chromatography 36 mg (20R)-5-cyano-21-phenyl-20-methyl-5α-pregn-8-en-3β-ol and 46 mg (20R)-5-cyano-21-phenyl-20-methyl-5α-pregn-8-en-3α-ol were isolated.

(20R)-5-Cyano-21-phenyl-20-methyl-5α-pregn-8-en-3β-ol

¹H-NMR (CDCl₃): δ=0.67 (s, 3H, H-18); 0.85 (d, J=7 Hz, 3H, H-21); 1.10 (s, 3H, H-19); 2.90 (dd, J=12 hz, J=3 Hz, 1H, H-21); 4.15 (broad-m, 1H, H-3); 7.12–7.30 (m, 5H, ph)

(20R)-5-Cyano-21-phenyl-20-methyl-5α-pregn-8-en-3α-ol $^1$H-NMR (CDCl$_3$): δ=0.65 (s, 3H, H-18); 0.84 (d, J=7 Hz, 3H, H-21); 1.05 (s, 3H, H-19); 2.90 (dd, J=12 hz, J=3 Hz, 1H, H-21); 4.12 (narrow-m, 1H, H-3); 7.12–7.30 (m, 5H, ph)

EXAMPLES 67+68

5-Cyano-24-nor-5α-cholest-8-en-3β-ol and 5-cyano-24-nor-5α-cholest-8-en-3α-ol a) 5-Cyano-3-(spiro-2',5'-dioxa-cyclopentyl)-24-nor-5α-cholest-8-ene 400 mg (20R)-5-cyano-3-(spiro-2',5'-dioxa-cyclopentyl)-5α-pregn-8-ene-20-methanol-4-methylbenzene sulfonate (example 63e) were treated with isobutyl magnesium bromide analoguously to example 63f. After column chromatography 206 mg 5-cyano-3-(spiro-2',5'-dioxa-cyclopentyl)-24-nor-5α-cholest-8-ene were isolated as a white solid.

$^1$H-NMR (CDCl$_3$): δ=0.62 (s, 3H, H-18); 0.85–0.95 (3×d, J=7 Hz); 1.10 (s, 3H, H-19); 3.88–4.10 (m, 4H, 3-ketal)

b) 5-Cyano-24-nor-5α-cholest-8-en-3-one 188 mg 5-cyano-3-(spiro-2',5'-dioxa-cyclopentyl)-24-nor-5α-cholest-8-ene were treated wit amberlyste 15 as described in example 63g. After filtration and evaporation of the solvent, 175 mg 5-cyano-24-nor-5α-cholest-8-en-3-one were isolated.

$^1$H-NMR (CDCl$_3$): δ=0.65 (s, 3H, H-18); 0.85–0.95 (3×d, J=7 Hz); 1.27 (s, 3H, H-19); 2.55 (pseudo-s, 2H)

c) 5-cyano-24-nor-5α-cholest-8-en-3β-ol and 5-cyano-24-nor-5α-cholest-8-en-3α-ol 1.73 mg 5-cyano-24-nor-5α-cholest-8-en-3-one were treated with 67 mg sodium borohydride as described in example 58b. After column chromatography, 35 mg 5-cyano-24-nor-5α-cholest-8-en-3β-ol and 64 mg 5-cyano-24-nor-5α-cholest-8-en-3α-ol were isolated.

5-Cyano-24-nor-5α-cholest-8-en-3β-ol $^1$H-NMR (CDCl$_3$): δ=0.60 (s, 3H, H-18); 0.85–0.95 (3×d, J=7 Hz); 1.10 (s, 3H, H-19); 4.13 (broad-m, 1H. H-3)

5-Cyano-24-nor-5α-cholest-8-en-3α-ol $^1$H-NMR (CDCl$_3$): δ=0.62 (s, 3H, H-18); 0.85–0.95 (3×d, J=7 Hz); 1.05 (s, 3H, H-19); 4.10 (broad-m, 1H, H-3)

EXAMPLES 69+70

5-Cyano-24-nor-5α-cholesta-8,23-dien-3β-ol and 5-cyano-24-nor-5α-cholesta-8,23-dien-3α-ol a) 5-Cyano-3-(spiro-2',5'-dioxa-cyclopentyl)-24-nor-5α-cholesta-8,23-diene 400 mg (20R)-5-cyano-3-(spiro-2',5'-dioxa-cyclopentyl)-5α-pregn-8-ene-20-methanol-4-methylbenzene sulfonate (example 63e) were treated with the grignard reagent from 1-bromo-2-methylpropene analoguously to example 63f. After column chromatography, 206 mg 5-cyano-3-(spiro-2', 5'-dioxa-cyclopentyl)-24-nor-5α-cholesta-8,23-diene were isolated as a white solid.

$^1$H-NMR (CDCl$_3$): δ=0.62 (s, 3H, H-18); 0.92 (d, J=7 Hz, 3H, H-21); 1.10 (s, 3H, H-19); 1.59, 1.70 (2×s, 2×3H); 3.90–4.10 (m, 4H, 3-ketal); 5.12 (t, J=7 Hz; 1H, H-23)

b) 5-Cyano-24-nor-5α-cholesta-8,23-dien-3-one 190 mg 5-cyano-3-(spiro-2', 5'-dioxa-cyclopentyl)-24-nor-5α-cholesta-8,23-diene were treated with amberlyste 15 as described in example 63g. After filtration and evaporation of the solvent, 170 mg 5-cyano-24-nor-5α-cholesta-8,23-dien-3-one were isolated.

$^1$H-NMR (CDCl$_3$): δ=0.60 (s, 3H, H-18); 0.90 (d, J=7 Hz, 3H, H-21); 1.10 (s,3H, H-19); 1.61, 1.72 (2×s, 2×3H); 2.55 (pseudo-s, 2H); 5.12 (t, J=7 Hz; 1H, H-23)

c) 5-Cyano-24-nor-5α-cholesta-8,23-dien-3β-ol and 5-cyano-24-nor-5α-cholesta-8,2-dien-3α-ol 170 mg 5-cyano-24-nor-5α-cholesta-8,23-dien-3-one were treated with 67 mg sodium borohydride as described in example 58b. After column chromatography and HPLC for purification, 8 mg 5-cyano-24-nor-5α-cholesta-8,23-dien-3β-ol and 19 mg 5-cyano-24-nor-5α-cholesta-8,23-dien-3α-ol were isolated.

5-Cyano-24-nor-5α-cholesta-8,23-dien-3β-ol $^1$H-NMR (CDCl$_3$): δ=0.60 (s, 3H, H-18); 0.90 (d, J=7 Hz, 3H, H-21); 1.10 (s,3H, H-19); 1.59, 1.72 (2×s, 2×3H); 4.13 (broad-m, 1H, H-3); 5.12 (t, J=7 Hz; 1H, H-23)

5-Cyano-24-nor-5α-cholesta-8,23-dien-3α-ol $^1$H-NMR (CDCl$_3$): δ=0.61 (s, 3H, H-18); 0.90 (d, J=7 Hz, 3H, H-21); 1.05 (s,3H, H-19); 1.59, 1.72 (2×s, 2×3H); 4.11 (narrow-m, 1H, H-3); 5.12 (t, J=7 Hz; 1H, H-23)

EXAMPLE 71

An agonistic oocyte assay can be performed as follows:

Oocytes were obtained from immature female mice (C57BU6J x DBA/2J F1, Bomholtgaard, Denmark) weighing 13–16 grams, that were kept under controlled temperature (20–22° C.), light (lights on 06.00–18.00) and relative humidity (50–70%). The mice received an intra-peritoneal injection of 0.2 ml gonadotropins (Gonal-F, Serono) containing 20 IU FSH and 48 hours later the animals were killed by cervical dislocation.

The ovaries were dissected out and the oocytes were isolated in Hx-medium (see below) under a stereo microscope by manual rupture of the follicles using a pair of 27 gauge needles. Spherical oocytes displaying an intact germinal vesicle (hereinafter designated GV) were divided in cumulus enclosed oocytes (hereinafter designated CEO) and naked oocytes (hereinafter designated NO) and placed in a-minimum essential medium (α-MEM without ribonucleosides, Gibco BRL, Cat. No. 22561) supplemented with 3 mg/ml bovine serum albumin (BSA, Sigma Cat. No. A-7030), 5 mg/ml human serum albumin (HSA, Statens Seruminstitute, Denmark), 0.23 mM pyruvate (Sigma, Cat. No S-8636), 2 mM glutamine (Flow Cat. No. 16-801), 100 IU/ml penicillin and 100 μg/ml streptomycin (Flow, Cat No. 16-700). This medium was supplemented with 3 mM hypoxanthine (Sigma Cat. No. H-9377) and designated Hx-medium.

The oocytes were rinsed three times in Hx-medium and oocytes of uniform size were divided into groups of CEO and NO. CEO and NO were cultured in 4-well multidishes (Nunclon, Denmark) in which each well contained 0.4 ml of Hx-medium. One control well (i.e., 35–45 oocytes cultured in identical medium with no addition of test compound) was always cultured simultaneously with 3 test wells (35–45 oocytes per well supplemented with test compound).

The oocytes were cultured in a humidified atmosphere of 5% $CO_2$ in air for 24 hours at 37° C. By the end of the culture period, the number of oocytes with germinal vesicle (hereinafter designated GV), germinal vesicle breakdown (hereinafter designated GVB) and polar bodies (hereinafter designated PB), respectively, were counted using a stereomicroscope (Wildt, Leica MZ 12). The percentage GVB, defined as percentage of oocytes undergoing GVB per total number of oocytes in that well, was calculated as:

% GVB=(number of GVB+number of PB/total number oocytes)×100.

The % PB was defined as percentage of oocytes displaying one extruded polar body per total number of oocytes in that well.

The effect of the tested compounds has been indexed against control level and 4,4-dimethyl-5α-cholesta-8,14,24-trien-3β-ol (hereinafter designated FF-MAS) where controls and FF-MAS are indexed to an effect of 0 and 100, respectively. The relative effect of the tested compound is calculated as follows:

Relative effect=((test GVB %−control GVB %)/(FF-MAS GVB %−control GVB %))×100.

Results

TABLE 1

The mean percentage GVB, the mean percentage PB and mean Relative Effect of compounds after culture of naked oocytes (NO) in vitro for 24 hours.

| | Concentration; mikroM | mean % GVB | mean % PB | mean Relative Effect |
|---|---|---|---|---|
| CONTROL | 0 | 11.9 | 5.5 | 0 |
| FF-MAS | 10 | 86.1 | 28.5 | 100 |
| Example 4 | 10 | 10.5 | 3.5 | −10 |
| Example 6 | 10 | 88 | 11 | 110 |
| Example 10 | 10 | 10 | 3 | −10 |
| Example 21 | 10 | 82 | 29.5 | 98 |
| Example 23 | 10 | 73.5 | 21.5 | 98 |
| Example 33 | 10 | 70 | 14.5 | 105 |

EXAMPLE 72

An antagonistic oocyte assay can be performed as follows:

Animals

Oocytes were obtained from immature female mice (C57BI/6J×DBA/2J F1-hybrids, Bomholtgaard, Denmark) weighing 13–16 grams, that were kept under controlled lighting and temperature. The mice received an intraperitoneal injection of 0.2 ml gonadotropins (Gonal F, Serono, Solna, Sweden, containing 20 IU FSH, alternatively, Puregon, Organon, Swords, Ireland containing 20 IU FSH) and 48 hours later the animals were killed by cervical dislocation.

Test of Meiosis-Inhibiting Substances in the Oocyte Test

The ovaries were dissected out and the oocytes were isolated in Hx-medium (see below) under a stereo microscope by manual rupture of the follicles using a pair of 27 gauge needles. Spherical, naked oocytes (NO) displaying an intact germinalvesicle (GV) were placed in α-minimum essential medium (α-MEM without ribonucleosides, Gibco BRL, Cat.No. 22561) supplemented with 3 mM hypoxanthine (Sigma Cat. No. H-9377), 8 mg/ml human serum albumin (HSA, Statens Seruminstitut, Denmark), 0.23 mM pyrubate (Sigma, Cat. No. S-8636), 2 mM glutamine (Flow Cat. No. 16-801), 100 IU/ml penicillin and 100 µg/ml streptomycin (Flow, Cat No. 16-700). This medium was designated Hx-medium.

Naked oocytes (NO) were rinsed three times in Hx-medium. 4,4-Dimethyl-5α-cholesta-8,14,24-trien-3β-ol (FF-MAS) has previously been shown to induce meiosis in NO in vitro (Byskov; A. G. et al Nature 374 (1995), 559–562). NO were cultured in Hx-medium supplemented with 5 µM FF-MAS in co-culture with the test compounds in different concentrations in 4-well multidishes (Nunclon, Denmark) in which each well contained 0.4 ml of the medium and 35–45 oocytes. One positive control (i.e., 35–45 oocytes cultured in Hx-medium containing FF-MAS with no addition of test compound) was always run simultaneously with the test cultures, which were supplemented with different concentrations of the compounds to be tested. In addition, one negative control (35–45 oocytes cultured in Hx-medium alone) was run simultaneously with the positive control.

Examination of Oocytes

By the end of the culture period, the number of oocytes with germinal vesicle (GV) or germinal vesicle breakdown (GVB) and those with polar body (PB) was counted using a stereomicroscope or an inverted microscope with differential interference contrast equipment. The percentage of oocytes with GVB+PB per total number of oocytes were calculated in the test cultures and in the control (positive and negative) culture groups. The relative inhibition of the test compound was calculated by the following formula:

Inhibition of test compound (in percentage)=100−
$[(GVB_{test\ compound}-GVB_{negative\ control})\times 100/(GVB_{positive\ control}-GVB_{negative\ control})]$.

In case of a dose response curve, an $IC_{50}$ (dose, which lead to a 50% inhibition) was calculated.

What is claimed is:

1. A method of regulating meiosis comprising administering to a subject in need thereof an effective amount of the compound of formula Ic;

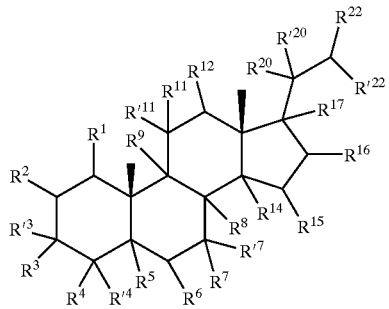

wherein $R^1$ is hydrogen, halogen, methyl, hydroxyl or oxo;

$R^2$ is selected from the group consisting of hydrogen, hydroxyl, $C_1$–$C_3$ alkyl, vinyl, $C_1$–$C_3$ alkoxy and halogen, or $R^2$ designates, together with $R^3$, an additional bond between the carbon atoms at which $R^2$ and $R^3$ are placed;

$R^3$ is selected from the group consisting of hydrogen, optionally substituted alkoxy, acyloxy, sulphonyloxy, phosphonyloxy, halogen, lower alkyl, and a perfluoro (lower alkyl) group; or $R^3$ designates, together with $R^2$ an additional bond between the two carbon atoms at which $R^2$ and $R^3$ are placed; or $R^3$ designates, together with $R'^3$, oxo or a group of the general formula =NOR$^{38}$ wherein $R^{38}$ is hydrogen or lower alkyl;

$R'^3$ designates hydrogen or hydroxy; with the proviso that $R^3$ and $R'^3$ are not, simultaneously, hydrogen;

$R^4$ and $R'^4$, which are different or identical with the proviso that they are not both hydroxyl, are selected from the group comprising hydrogen, halogen, hydroxy and $C_1-C_6$ alkyl which may be substituted by halogen, hydroxy or cyano, or wherein $R^4$ and $R'^4$ together designate methylene or oxo or, together with the carbon atom to which they are bound, form a cyclopropane ring, a cyclopentane ring, or a cyclohexane ring; or $R^4$ designates, together with $R'^4$ and $R^5$, a methano bridge between the carbon atoms in 4 and 5 position or an additional bond between the carbon atoms in 4 and 5 position;

$R^5$ is hydrogen, halogen, hydroxyl, lower alkyl, cyano, hydroxymethyl, a carbaldehyde, an oxime derived from a carbaldehyde, a carboxylic acid, a primary or secondary amide derived from a carboxylic acid, an ester with a $C_1-C_6$-alcohol group; or $R^5$ designates, together with $R^6$, an additional bond between the carbon atoms at which $R^5$ and $R^6$ are placed;

$R^6$ is hydrogen, hydroxyl, halogen or oxo, or $R^6$ designates, together with $R^5$ or $R^7$, an additional bond between the carbon atoms at which $R^6$ and $R^5$ or $R^7$ are placed;

$R^7$ is selected from the group consisting of hydrogen, hydroxyl, lower alkoxy, acyloxy, halogen and lower alkyl or $R^7$ designates, together with $R^6$ or $R^8$, an additional bond between the carbon atoms at which $R^7$ and $R^6$ or $R^8$ or are placed;

$R'^7$ is hydrogen, or, if $R^7$ is lower alkyl, $R'^7$ is hydrogen or hydroxy; or $R^7$ designates, together with $R'^7$, methylene, oxo or a group of the general formula $=NOR^{36}$, wherein $R^{36}$ is hydrogen or lower alkyl;

$R^8$ is hydrogen, hydroxy or halogen, or $R^8$ designates, together with $R^7$, $R^9$ or $R^{14}$, an additional bond between the carbon atoms at which $R^8$ and $R^7$, $R^9$ or $R^{14}$ are placed;

$R^9$ is hydrogen, hydroxy or halogen, or $R^9$ designates, together with $R^8$ or $R^{11}$, an additional bond between the carbon atoms at which $R^9$ and $R^8$ or $R^{11}$ are placed;

$R^{11}$ is selected from the group consisting of hydrogen, hydroxyl, lower alkoxy, acyloxy, halogen and lower alkyl, or $R^{11}$ designates, together with $R^9$ or $R^{12}$, an additional bond between the carbon atoms at which $R^{11}$ and $R^9$ or $R^{12}$ are placed;

$R^{11}$ is hydrogen or, if $R^{11}$ is lower alkyl, $R'^{11}$ is hydrogen or hydroxyl, or $R^{11}$ designates, together with $R'^{11}$, methylene, oxo or a group of the general formula $=NOR^{37}$, wherein $R^{37}$ is hydrogen or lower alkyl;

$R^{12}$ is selected from the group consisting of hydrogen, halogen, $C_1-C_4$ alkyl, methylene, hydroxyl, lower alkoxy, acyloxy, oxo and a group of the general formula $=NOR^{33}$ wherein $R^{33}$ is hydrogen or $C_1-C_3$ alkyl, or $R^{12}$ designates, together with $R^{11}$, an additional bond between the carbon atoms at which $R^{11}$ and $R^{12}$ are placed;

$R^{14}$ is hydrogen or hydroxyl, or $R^{14}$ designates, together with $R^{15}$, an additional bond between the carbon atoms at which $R^{14}$ and $R^{15}$ are placed;

$R^{15}$ is selected from the group consisting of hydrogen, halogen, lower alkyl, methylene, hydroxyl, lower alkoxy, oxo and a group of the general formula $=NOR^{32}$ wherein $R^{32}$ is hydrogen or $C_1-C_3$ alkyl, or $R^{15}$ designates, together with $R^{14}$ an additional bond between the carbon atoms at which $R^{15}$ and $R^{14}$ are placed;

$R^{16}$ is selected from the group consisting of hydrogen, halogen, $C_1-C_3$ alkyl, methylene, hydroxyl, lower alkoxy, oxo and a group of the general formula $=NOR^{34}$ wherein $R^{34}$ is hydrogen or lower alkyl, or $R^{16}$ designates, together with $R^{17}$, an additional bond between the carbon atoms at which $R^{16}$ and $R^{17}$ are placed;

$R^{17}$ is hydrogen or hydroxyl, or $R^{17}$ designates, together with $R^{16}$, an additional bond between the carbon atoms at which $R^{17}$ and $R^{16}$ are placed;

$R^{20}$ is selected from the group consisting of hydrogen, lower alkyl and hydroxy-methyl, or $R^{20}$ and $R'^{20}$ together designate methylene or oxo;

$R'^{20}$ is hydrogen, halogen, lower alkyl or hydroxy;

$R'^{22}$ is hydrogen, hydroxy or oxo;

$R^{22}$ is cyclohexyl or cyclohexylalkyl, each optionally substituted by one or more of the following groups which substituents may be different or identical: hydroxyl, lower alkoxy, halogen, amino, cyano, carboxy, a group of the general formula $—COOR^{39}$, oxo, N-alkylamino or N,N-dialkylamino wherein the N-alkylamino or N,N-dialkylamino substituent optionally is substituted by carboxy, lower alkoxy or lower alkylthio; and wherein $R^{39}$ is lower alkyl or aralkyl.

2. The method of claim 1, wherein meiosis is regulated in a mammalian germ cell.

3. The method of claim 1, wherein the compound is administered to a germ cell located in a mammalian host.

4. The method of claim 3, wherein the germ cell is an oocyte.

5. The method of claim 1, wherein the compound is administered to an oocyte ex vivo or in vitro.

6. The method of claim 3, wherein the germ cell is a male germ cell.

7. The method of claim 6, wherein the compound is administered to testicular tissue in vivo, ex vivo or in vitro.

* * * * *

UNITED STATES PATENT AND TRADEMARK OFFICE
CERTIFICATE OF CORRECTION

PATENT NO. : 6,884,796 B2 Page 1 of 1
APPLICATION NO. : 10/162843
DATED : April 26, 2005
INVENTOR(S) : Faarup et al.

It is certified that error appears in the above-identified patent and that said Letters Patent is hereby corrected as shown below:

Column 53, line 44, claim 1:
"$R^{11}$ is hydrogen" should read --$R^{'11}$ is hydrogen--.

Signed and Sealed this

Thirty-first Day of July, 2007

JON W. DUDAS
*Director of the United States Patent and Trademark Office*